United States Patent
Schraga

(10) Patent No.: US 9,700,681 B2
(45) Date of Patent: Jul. 11, 2017

(54) PEN NEEDLE WITH QUICK RELEASE AND/OR REMOVAL SYSTEM

(75) Inventor: Steven Schraga, Surfside, FL (US)

(73) Assignee: STAT MEDICAL DEVICES, INC., North Miami, FL (US)

(*) Notice: Subject to any disclaimer, the term of this patent is extended or adjusted under 35 U.S.C. 154(b) by 829 days.

(21) Appl. No.: 12/779,472

(22) Filed: May 13, 2010

(65) Prior Publication Data

US 2010/0292654 A1    Nov. 18, 2010

Related U.S. Application Data

(60) Provisional application No. 61/178,673, filed on May 15, 2009.

(51) Int. Cl.
| | | |
|---|---|---|
| *A61M 5/34* | (2006.01) | |
| *A61M 5/32* | (2006.01) | |
| *A61M 39/10* | (2006.01) | |

(52) U.S. Cl.
CPC ............ *A61M 5/326* (2013.01); *A61M 5/347* (2013.01); *A61M 5/3202* (2013.01); *A61M 5/3205* (2013.01); *A61M 2005/3246* (2013.01); *A61M 2005/3247* (2013.01); *A61M 2005/3267* (2013.01); *A61M 2039/1016* (2013.01); *A61M 2039/1027* (2013.01)

(58) Field of Classification Search
CPC .. A61M 2005/3246; A61M 2005/3254; A61M 5/326; A61M 5/347; A61M 5/3202; A61M 2005/3267
USPC ........ 604/110, 181, 187, 239–243, 131, 139, 604/263, 192, 198, 195, 232
See application file for complete search history.

(56) References Cited

U.S. PATENT DOCUMENTS

| | | | |
|---|---|---|---|
| 445,602 | A | 2/1891 | Richards |
| 4,894,055 | A | 1/1990 | Sudnak |
| 4,909,792 | A | 3/1990 | Norelli |
| 4,973,318 | A | 11/1990 | Holm et al. |
| 5,226,894 | A * | 7/1993 | Haber et al. .................. 604/198 |
| 5,242,401 | A | 9/1993 | Colsky |

(Continued)

FOREIGN PATENT DOCUMENTS

| | | |
|---|---|---|
| WO | 99/08742 | 2/1999 |
| WO | 00/69501 | 11/2000 |
| WO | WO 2008/077706 | * 7/2008 |

OTHER PUBLICATIONS

"Usage Instructions", NovoLog Mix 70/30 Flex Pen; 2 pages.

*Primary Examiner* — Matthew F Desanto
(74) *Attorney, Agent, or Firm* — Thomas | Horstemeyer LLP; Randy R. Schoen

(57) ABSTRACT

An injection device tip includes a body configured to be removably connected to an injection device and a needle having a portion projecting from a proximal end of the body. The body at least one of has flexible portions which can be deflected inwardly to cause release of an engagement between the body and a proximal end of the injection device, has two oppositely arranged flexible portions arranged outside an imaginary circle defined by an outside surface of two opposite portions arranged between the two oppositely arranged flexible portions, is generally oval in shape, is generally rectangular in shape, is generally square in shape, and is non-circular in shape. This Abstract is not intended to define the invention disclosed in the specification, nor intended to limit the scope of the invention in any way.

25 Claims, 34 Drawing Sheets

(56) References Cited

U.S. PATENT DOCUMENTS

| | | |
|---|---|---|
| 5,242,416 A | 9/1993 | Hutson |
| 5,389,085 A | 2/1995 | D'Alessio et al. |
| 5,419,773 A | 5/1995 | Rupp |
| 5,454,828 A | 10/1995 | Schraga |
| 5,591,138 A | 1/1997 | Vaillancourt |
| 5,593,387 A | 1/1997 | Rupp |
| 5,611,786 A * | 3/1997 | Kirchhofer ............ A61M 5/348 604/232 |
| 5,980,488 A | 11/1999 | Thorne |
| 6,117,108 A | 9/2000 | Woehr et al. |
| 6,287,278 B1 | 9/2001 | Woehr et al. |
| 6,379,333 B1 | 4/2002 | Brimhall et al. |
| 6,391,003 B1 | 5/2002 | Lesch, Jr. |
| 6,460,234 B1 | 10/2002 | Gianchandani |
| 6,470,754 B1 | 10/2002 | Gianchandani |
| 6,616,630 B1 | 9/2003 | Woehr et al. |
| 6,652,490 B2 | 11/2003 | Howell |
| 6,749,588 B1 | 6/2004 | Howell et al. |
| 6,855,129 B2 | 2/2005 | Jensen et al. |
| 7,125,397 B2 | 10/2006 | Woehr et al. |
| 7,214,211 B2 | 5/2007 | Woehr et al. |
| 7,264,613 B2 | 9/2007 | Woehr et al. |
| 7,462,168 B2 * | 12/2008 | Stonehouse ............ A61M 5/326 604/192 |
| 7,540,858 B2 | 6/2009 | DiBiasi |
| 7,553,293 B2 | 6/2009 | Jensen et al. |
| 7,871,397 B2 | 1/2011 | Schraga |
| 8,016,797 B2 * | 9/2011 | Gratwohl ............ A61M 5/326 604/163 |
| 2002/0004648 A1 | 1/2002 | Larsen et al. |
| 2002/0133122 A1 | 9/2002 | Giambattista et al. |
| 2003/0014018 A1 | 1/2003 | Giambattista et al. |
| 2003/0105431 A1 | 6/2003 | Howell |
| 2003/0195471 A1 | 10/2003 | Woehr et al. |
| 2004/0111067 A1 * | 6/2004 | Kirchhofer ............ A61M 5/24 604/240 |
| 2004/0116856 A1 | 6/2004 | Woehr et al. |
| 2004/0186434 A1 | 9/2004 | Harding et al. |
| 2004/0204681 A1 | 10/2004 | Thoresen et al. |
| 2004/0236284 A1 | 11/2004 | Hoste et al. |
| 2004/0236288 A1 | 11/2004 | Howell et al. |
| 2005/0004532 A1 | 1/2005 | Woehr et al. |
| 2005/0038392 A1 | 2/2005 | DeSalvo |
| 2005/0080378 A1 | 4/2005 | Cindrich et al. |
| 2005/0107748 A1 | 5/2005 | Thorne et al. |
| 2005/0277881 A1 | 12/2005 | Sibbitt, Jr. |
| 2005/0277895 A1 | 12/2005 | Giambattista et al. |
| 2005/0283115 A1 * | 12/2005 | Giambattista et al. ....... 604/110 |
| 2006/0229652 A1 | 10/2006 | Iio et al. |
| 2006/0264828 A1 * | 11/2006 | Woehr et al. ................. 604/110 |
| 2007/0049868 A1 | 3/2007 | Woehr et al. |
| 2007/0083159 A1 | 4/2007 | Woehr et al. |
| 2007/0100297 A1 | 5/2007 | Woehr et al. |
| 2007/0129689 A1 | 6/2007 | Woehr et al. |
| 2007/0203458 A1 | 8/2007 | Tsubota |
| 2008/0108951 A1 | 5/2008 | Jerde et al. |
| 2008/0154192 A1 | 6/2008 | Schraga |
| 2008/0177237 A1 | 7/2008 | Stonehouse et al. |
| 2008/0177238 A1 | 7/2008 | Follman et al. |
| 2009/0069753 A1 * | 3/2009 | Ruan et al. ................... 604/192 |
| 2010/0292654 A1 | 11/2010 | Schraga |
| 2011/0022001 A1 | 1/2011 | Wei |
| 2011/0077615 A1 | 3/2011 | Schraga |
| 2011/0106016 A1 | 5/2011 | Wei |
| 2011/0118667 A1 | 5/2011 | Zaiken et al. |
| 2011/0160675 A1 | 6/2011 | Ruan et al. |

\* cited by examiner

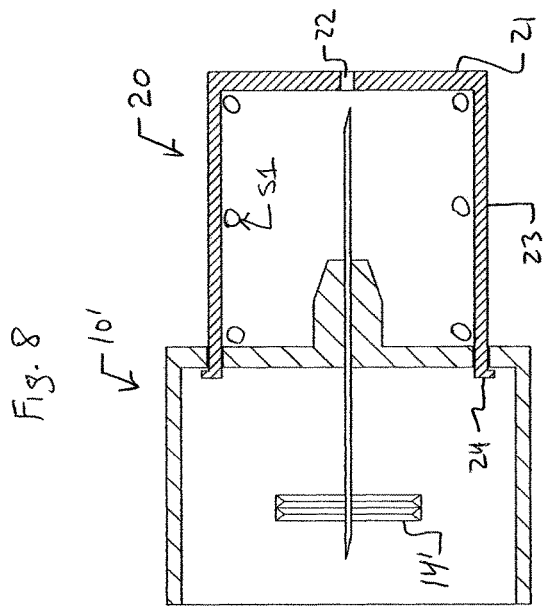
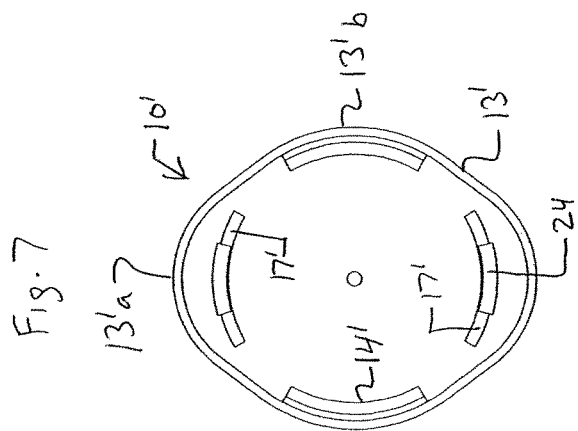

Fig. 9
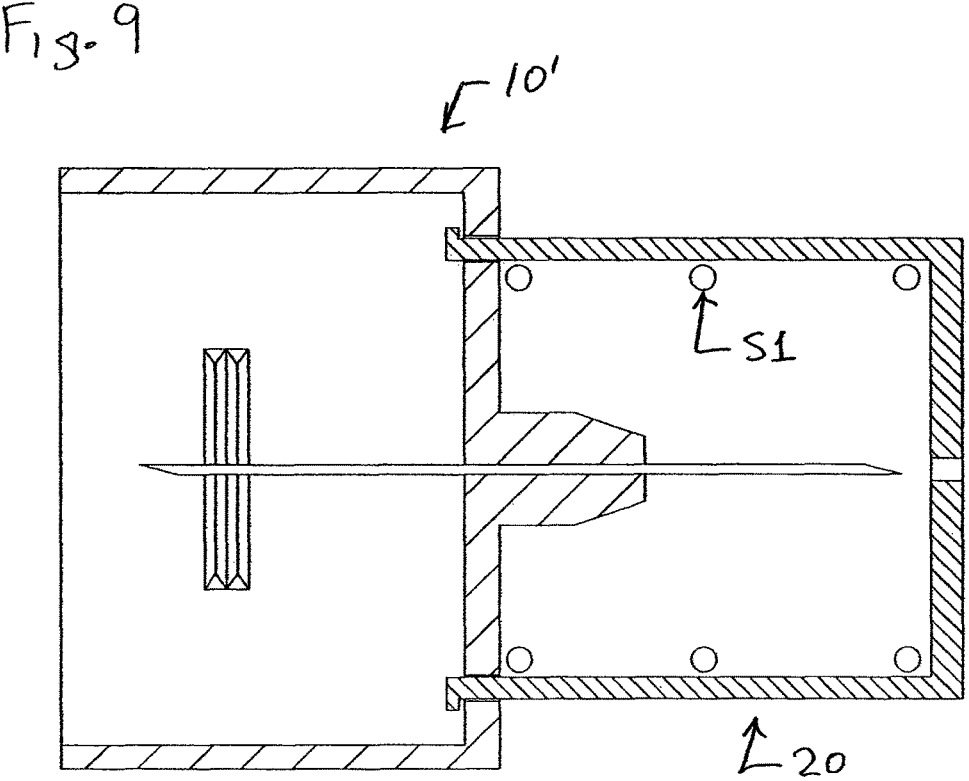
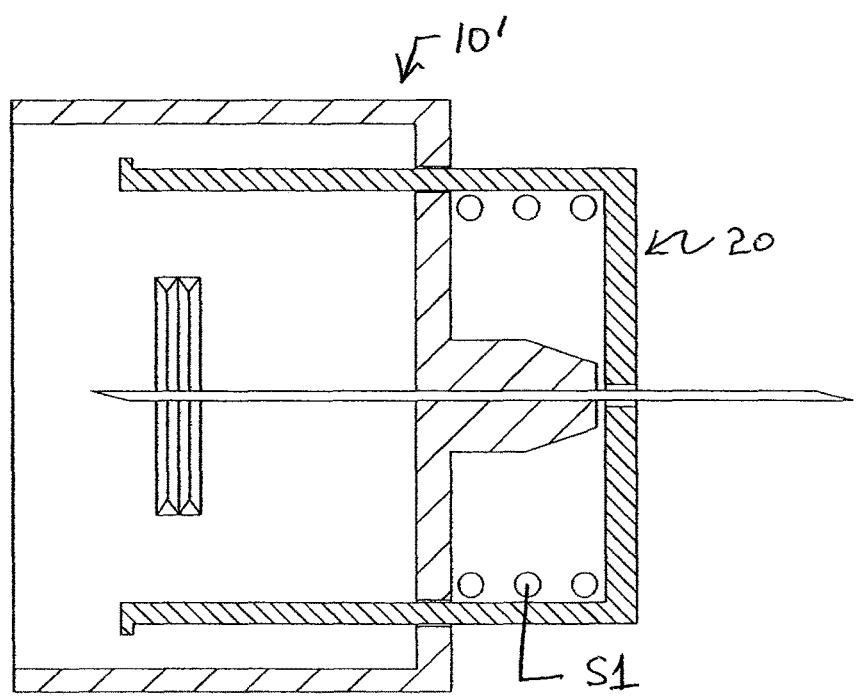
Fig. 10

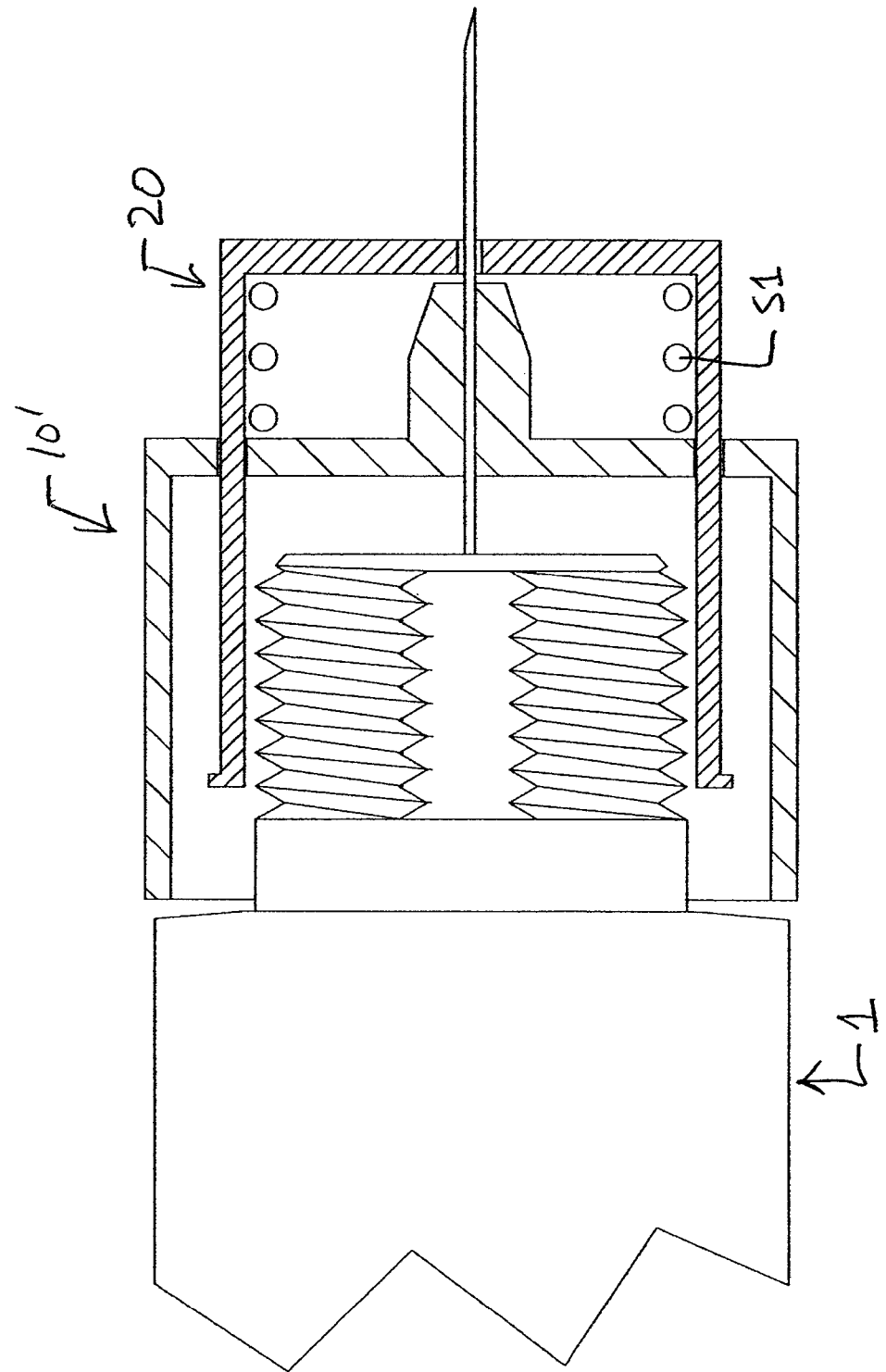

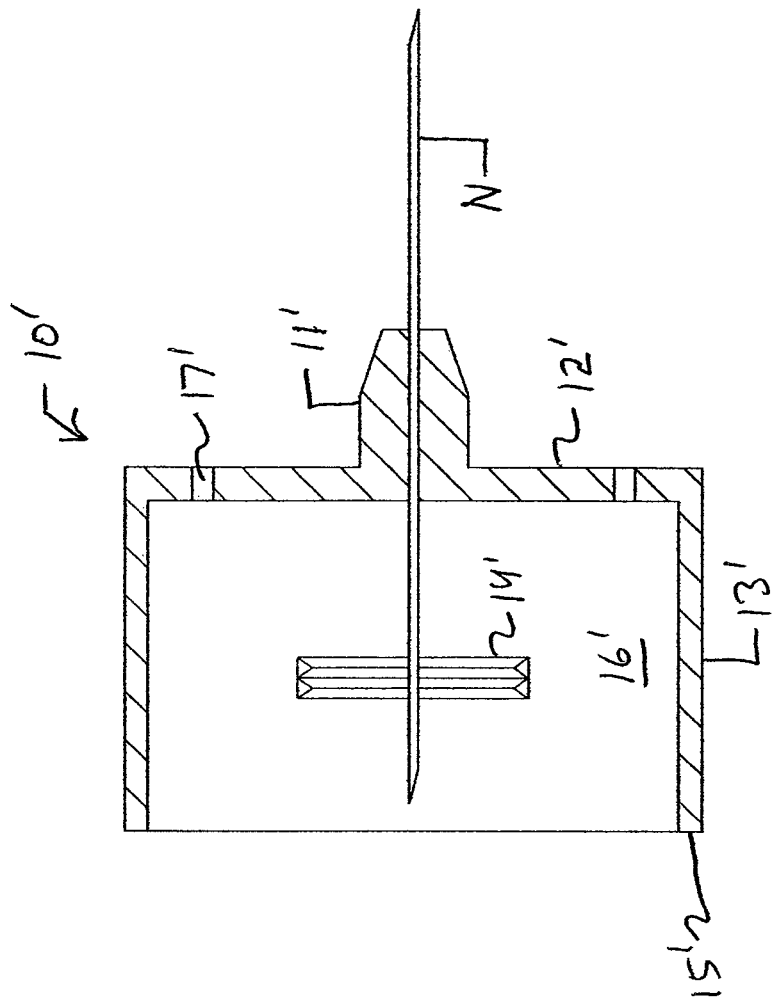
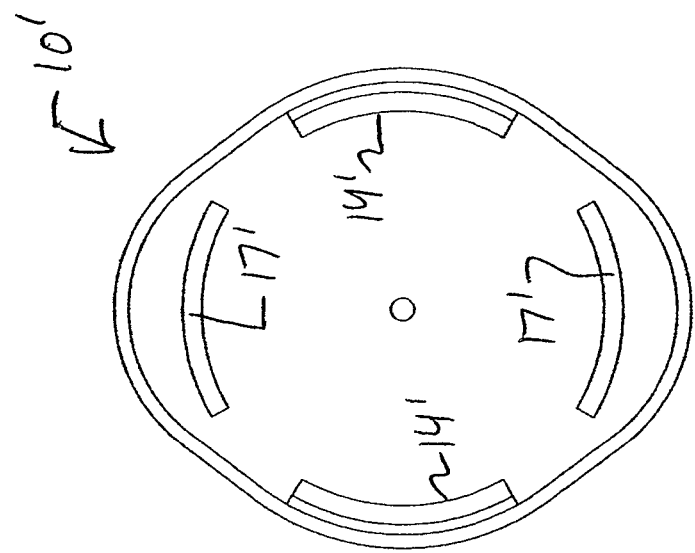

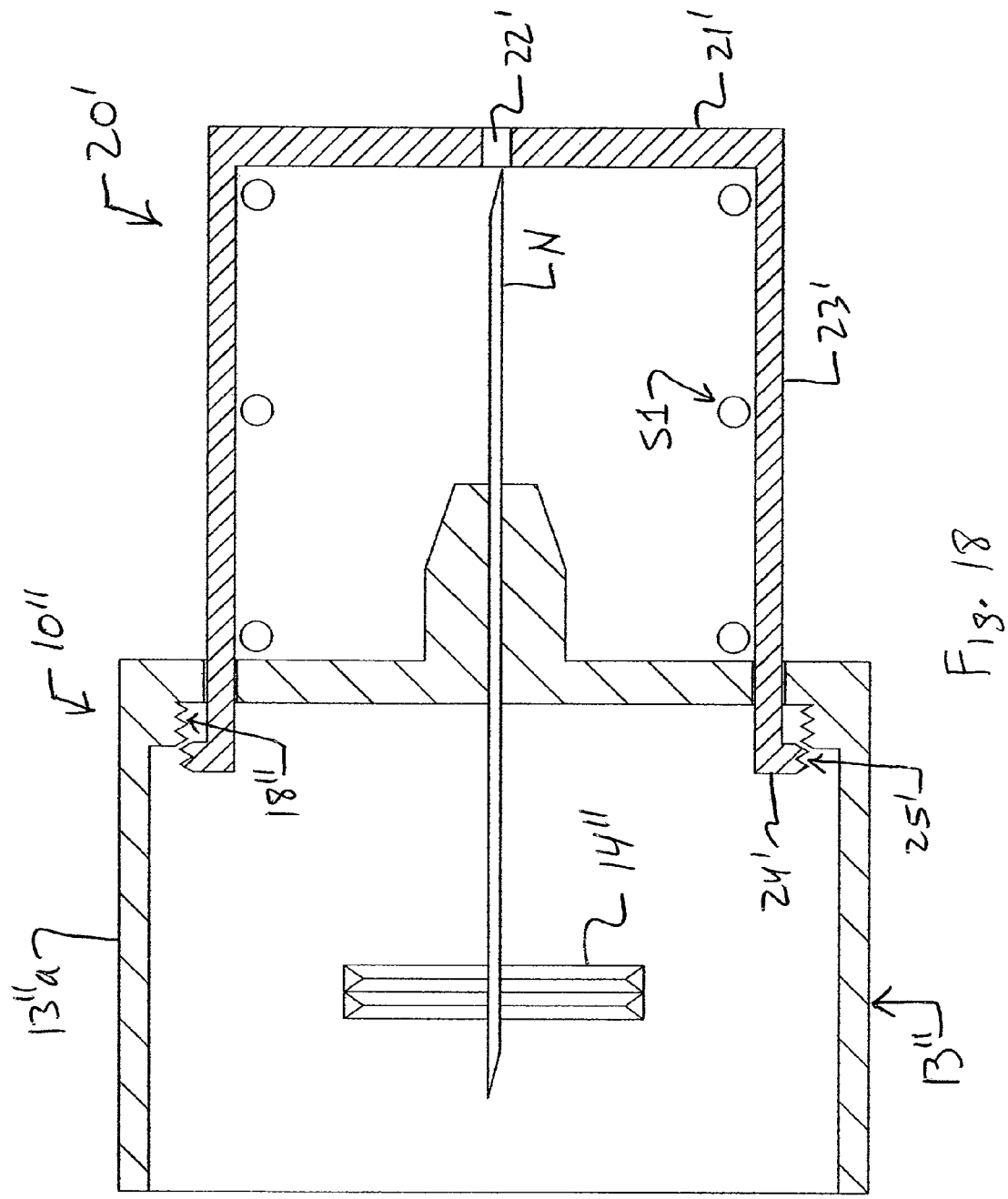

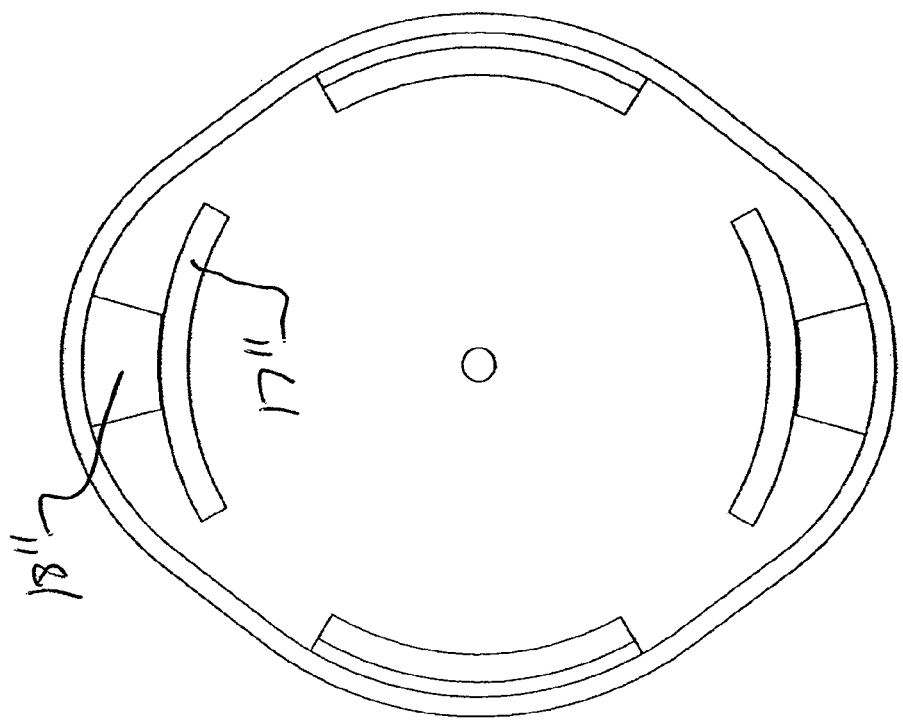
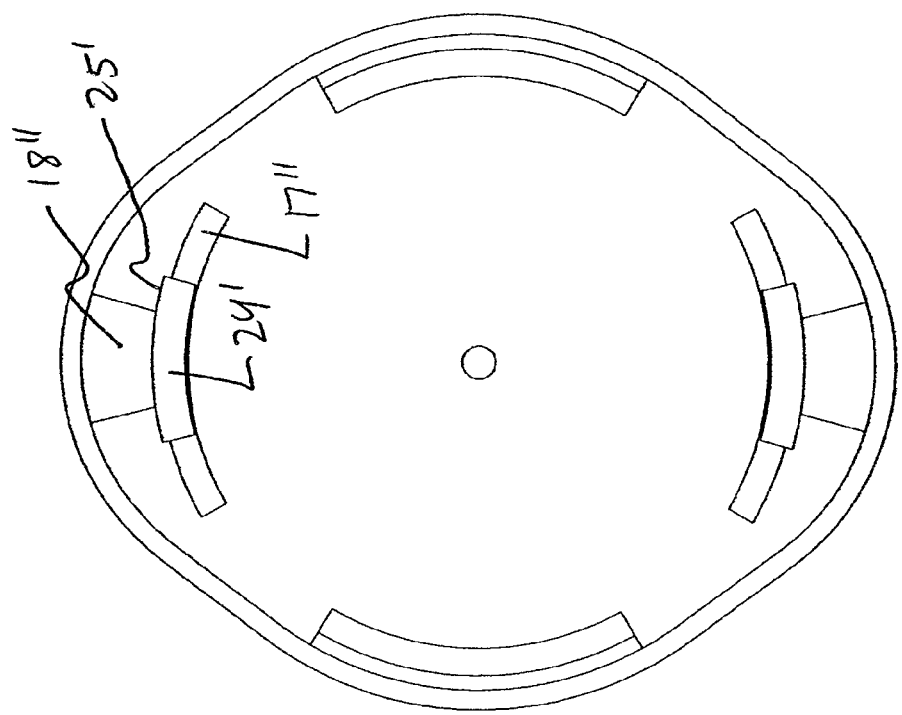

Fig. 26
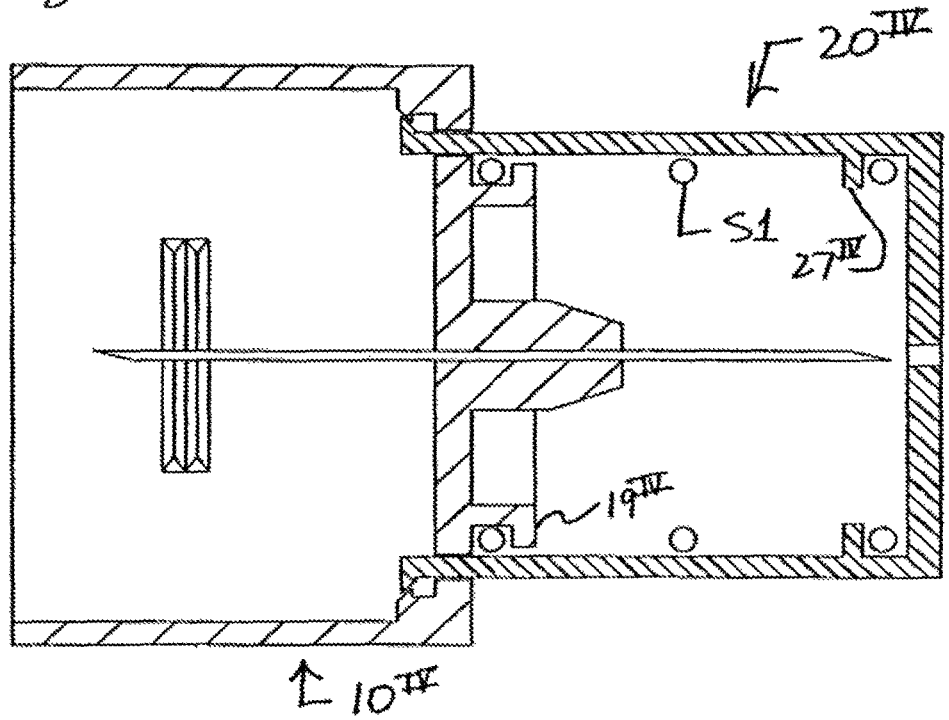
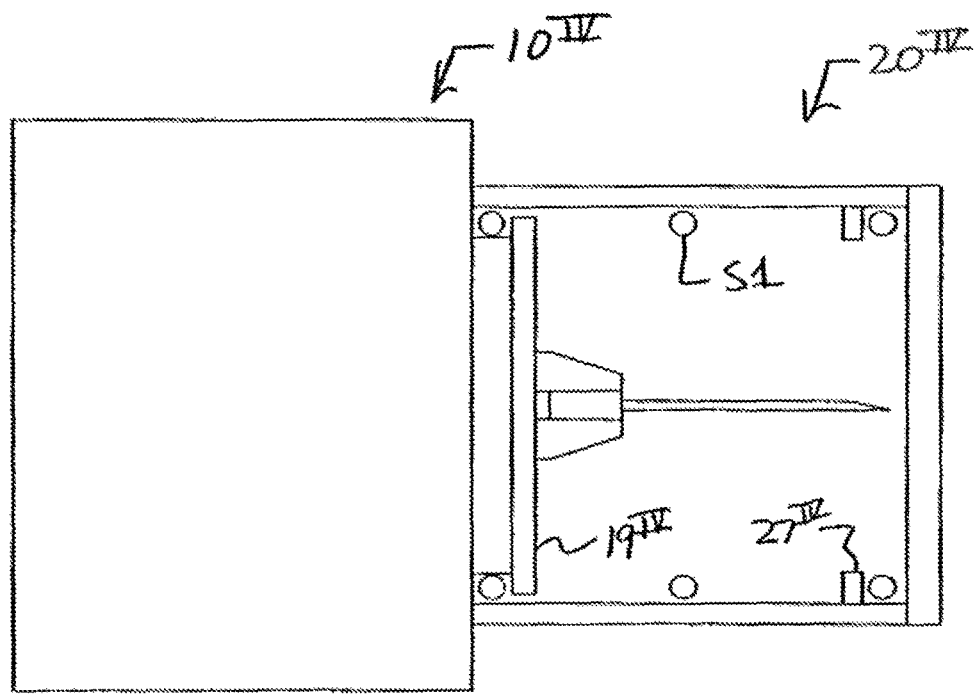
Fig. 27

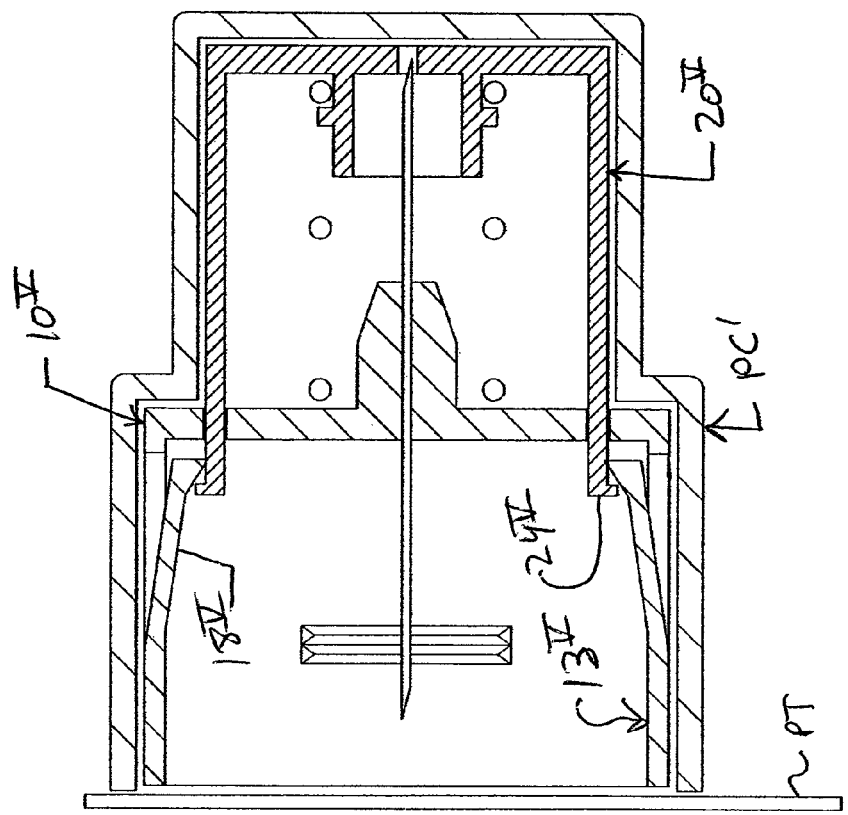
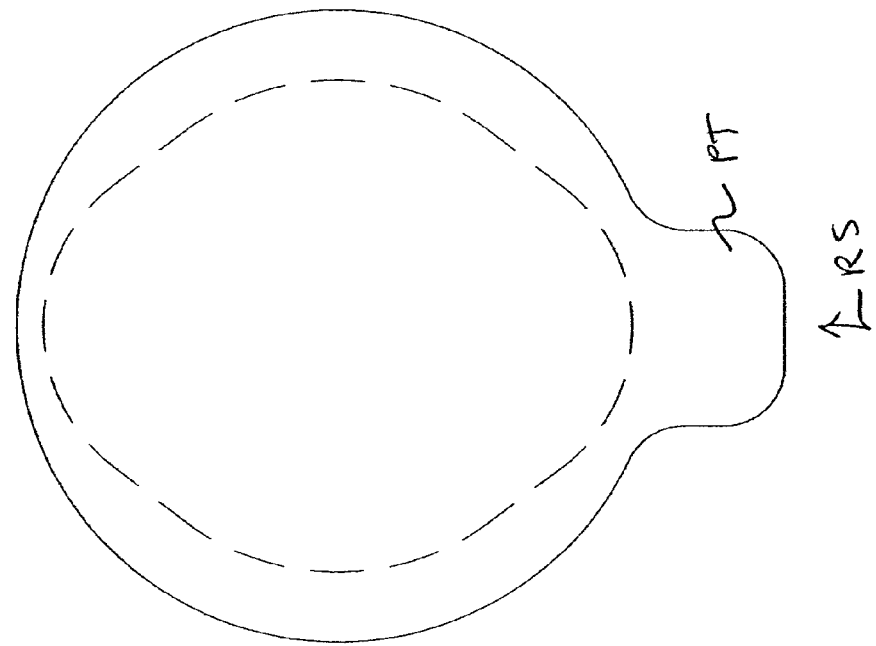

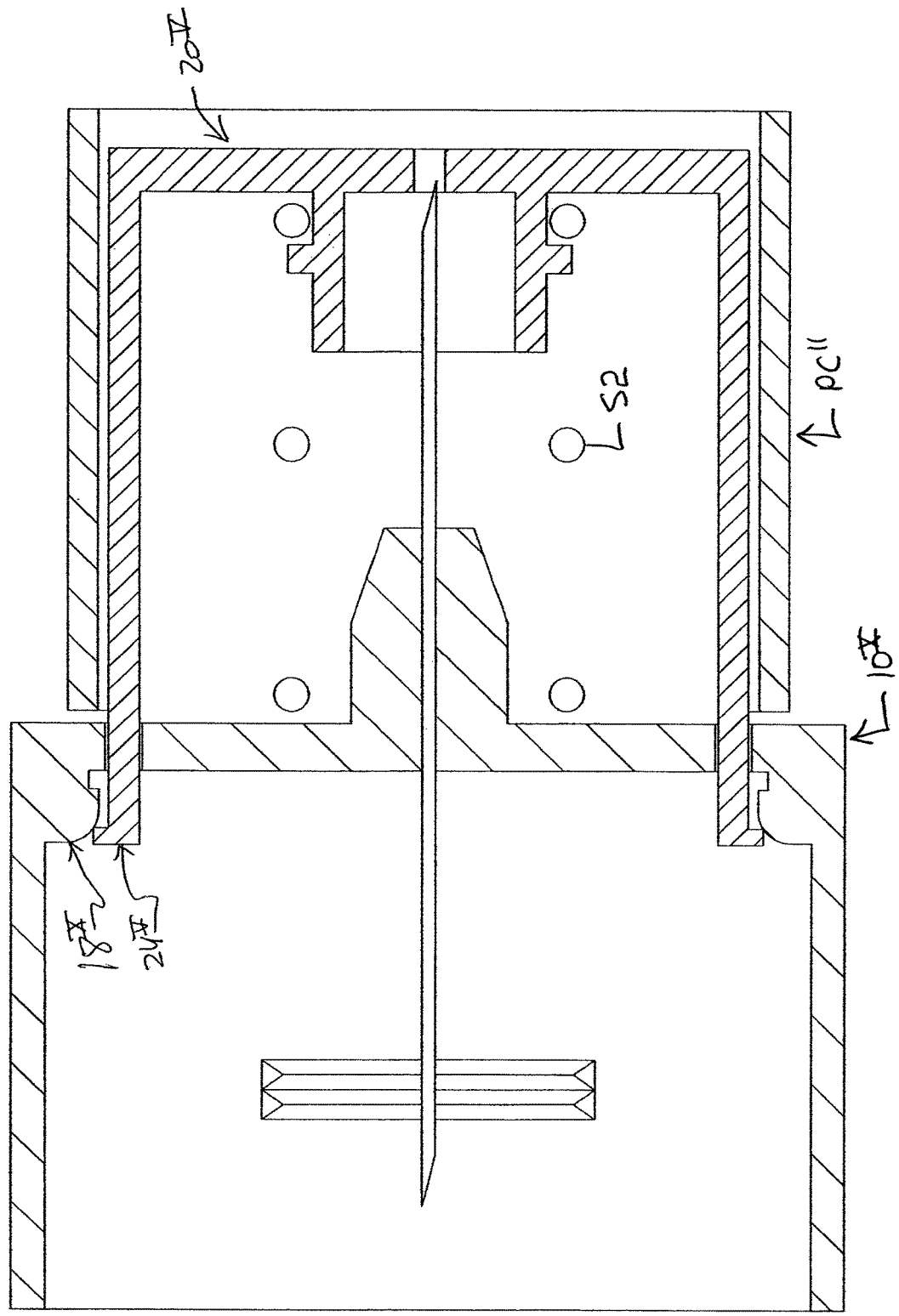

PEN NEEDLE WITH QUICK RELEASE AND/OR REMOVAL SYSTEM

CROSS-REFERENCE TO RELATED APPLICATIONS

The instant application is a US non-provisional Application based on U.S. provisional application No. 61/178,673, filed May 15, 2009, the disclosure of which is hereby expressly incorporated by reference hereto in its entirety.

BACKGROUND OF THE INVENTION

1. Field of the Invention

This invention relates generally to pen injection devices, e.g., pre-loaded syringes, such as are utilized for injection of medicament into the body tissues of human and animal patients. More specifically, this invention relates to a removable pen needle which is more easily removed from the pen injection device. The pen needle can preferably include a safety system or shield to prevent inadvertent pricking on a user.

This invention also relates to a method of using pen needles for pen injection devices wherein the pen needle is configured to be used with conventional the pen injection device.

This invention also relates to a method of using pen injection devices more safely, i.e., preventing the user from being pricked when handling and/or attempting to remove the pen needle from the pen injection device.

2. Discussion of Background Information

U.S. Pat. No. 4,973,318, the disclosure of which is hereby expressly incorporated by reference in its entirety, discloses a disposable syringe includes first and second housing elements which are coupled together for rotation without axial movement therebetween. The first housing element receives a cartridge of a solution to be injected, and mounts a liquid outlet needle at its front end. A piston rod is disposed in the second housing element to move axially therein, and this piston rod includes a rod element and a nut element. The rod element is coupled to the first housing element to move axially therein without relative rotation therewith, and the nut element is threaded to the rod element for telescoping movement therewith and is configured to move axially in the second housing element without relative rotation therein. A pressure receiving element is mounted on the nut element. The housing, rod, nut and pressure receiving elements cooperate such that relative rotation between the housing elements in a selected direction causes relative rotation between the nut and rod elements and thereby increases the effective length of the piston rod and causes the pressure receiving element to extend from the second housing element. A protective cap is removably mounted over the first housing element and is configured to abut second housing element while mounted in place on the first housing element. This protective cap is engaged with the first housing element such that rotation of the cap with respect to the second housing element causes rotation of the first housing element with respect to the second housing element.

This type of syringe is shown in FIGS. 1 and 2 wherein the pre-loaded syringe 1 has a proximal threaded end 2 which is configured to accept a needle tip assembly consisting of a needle tip 5, a needle tip cover, and a needle cover. A user installs the needle tip assembly 5 onto the end 2, after removing the assembly from its individual package, onto the threaded proximal end 2 by simply sliding it onto the end 2 axially. Because internal threads of the needle tip 5 are mounted to radially deflectable members, installation over threads of the end 2 occurs with a ratchet effect. This installation is made safe by the covers which ensure that the user will not be pricked by the needle N. Once installed, the user can remove the needle tip cover by simply sliding it off axially. Next, the user can remove the needle cover to expose the needle N. The pen needle device is then made ready for use in providing an injection to the user. After injection, the user will typically remove the needle tip 5 and discard the same. To accomplish the removal, the user will typically reinstall the needle tip cover and rotate it to cause the needle tip to unthread from the threaded end 2 (some users may even install the needle cover prior to installing the cover). Once removed, however, it is still possible to reinstall the used needle tip 5 by simply repeating the steps noted above. Unless the user discards the needle tip 5, it is possible that she or other users will not remember or know that it has already been used. That is, there is nothing to prevent reuse of the needle tip 5 should someone attempt to reinstall the needle tip onto the end 2. Furthermore, if the user is unable to locate the covers (i.e., if they have become lost), he/she must then attempt to grip the needle tip 5 in order to unthread it from the end 2. As is apparent, this action can be risky because the user can possibly inadvertently be pricked by the needle N either in attempting to properly grip the needle tip 5, in the action of rotating it to the point it is removed, or even in the handling of the needle tip 5 after it has been removed and prior to being properly discarded. Still further, if the needle tip 5 is not properly discarded (such as being correctly placed in a sharps container), others may come in contact with the needle tip 5 and possibly become injured thereby.

It is therefore desirable to provide a pen needle system which is safer to use compared to the conventional devices discussed above and/or which does not have one or more of the above-noted disadvantageous.

SUMMARY OF THE INVENTION

According to one non-limiting embodiment of the invention, there is provided an injection device tip comprising a body configured to be removably connected to an injection device and a needle having a portion projecting from a proximal end of the body. The body at least one of has flexible portions which can be deflected inwardly to cause release of an engagement between the body and a proximal end of the injection device, has two oppositely arranged flexible portions arranged outside an imaginary circle defined by an outside surface of two opposite portions arranged between the two oppositely arranged flexible portions, is generally oval in shape, is generally rectangular in shape, is generally square in shape, and is non-circular in shape.

The needle may be a double-ended having one end projection from the proximal end of the body. The body may comprise at least one projection for engaging an external thread of the proximal end of the injection device. Once installed, the tip may threadably engage with the proximal end of the injection device. The body may comprise at least one partial internal thread section for engaging an external thread of the proximal end of the injection device. The body may comprise at least two oppositely arranged partial internal thread sections for engaging an external thread of the proximal end of the injection device. The body may include the flexible portions which can be deflected inwardly to cause release of an engagement between the body and a proximal end of the injection device and is generally oval in shape. The body may include the flexible portions which can be deflected inwardly to cause release of an engagement between the body and a proximal end of the injection device and is generally non-circular in shape. The body may include the flexible portions which can be deflected inwardly to cause release of an engagement between the body and a proximal end of the injection device and is generally non-circular in shape. The body may include the two oppositely arranged flexible portions arranged outside an imaginary circle defined by an outside surface of two opposite portions arranged between the two oppositely arranged flexible portions and is generally oval in shape. The body may include the two oppositely arranged flexible portions arranged outside an imaginary circle defined by an outside surface of two opposite portions arranged between the two oppositely arranged flexible portions and is generally non-circular in shape.

The tip may further comprise a safety shield adapted to cover the needle. The tip may further comprise a safety shield movably mounted to the body and being adapted to cover the needle. The tip may further comprise a safety shield movably mounted to the proximal end of the body.

The tip may further comprise a safety shield arranged on the proximal end of the body. The safety shield may be movable at least between an initial position and an extended position. The initial position and the extended position may each cover a free end of the needle. The safety shield may be movable at least between an initial position, a retracted position, and an extended position. The initial position may cover a free end of the needle and the retracted position may expose a free end of the needle. The extended position may cover a free end of the needle and the retracted position may expose a free end of the needle. The initial position may cover a free end of the needle, the retracted position may expose a free end of the needle, and the extended position may prevent re-use of the tip. The retracted position may expose a free end of the needle and, in the extended position, the safety shield may be one of locked and non-movably retained.

The invention also provides for a method of removing the tip of the type described above, wherein the method comprises installing the tip onto a proximal end of an injection device and removing the tip by applying a squeezing force to opposite sides of the body.

The invention also provides for a pre-filled injection device comprising at least one feature of the tip shown in at least one drawing of the instant application.

The invention also provides for a pre-filled injection device comprising a pre-filled injection device body and a removable pen needle installed on the pre-filled injection device body. The pen needle at least one of has flexible portions which can be deflected inwardly to cause release of an engagement between the body and a proximal end of the injection device, has two oppositely arranged flexible portions arranged outside an imaginary circle defined by an outside surface of two opposite portions arranged between the two oppositely arranged flexible portions, is generally oval in shape, is generally rectangular in shape, is generally square in shape, and is non-circular in shape.

The invention also provides for a pen needle comprising a body configured to be removably connected to an injection device, a needle having a portion projecting from a proximal end of the body, and the body comprising deflectable or flexible portions which can be deflected inwardly to cause release of an engagement between the body and a proximal end of the injection device. The deflectable or flexible portions are arranged outside an imaginary circle defined by an outside surface of at least one other portion of the body.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 7 shows a rear end view of a second non-limiting embodiment of a pen needle or tip assembly according to the invention;

FIG. 8 shows a side cross-section view of the pen needle or tip assembly shown in FIG. 7. The hollow needle is not shown in cross-section;

FIGS. 9 and 10 show side cross-section views of the pen needle or tip assembly of FIGS. 7 and 8 with the safety-shield being in an initial or extended position (FIG. 9) and a using or retracted position (FIG. 10). This embodiment is similar to the first embodiment but additionally includes a safety-shield and spring;

FIG. 12 shows another side cross-section view of FIG. 11 except that the safety-shield is in the retracted position;

FIG. 13 shows a rear end view of the pen needle or tip assembly of FIGS. 7 and 8 with the safety-shield removed;

FIG. 14 shows a side cross-section view of the pen needle or tip assembly shown in FIG. 13. The hollow needle is not shown in cross-section;

FIG. 18 shows a side cross-section view of another non-limiting embodiment of a pen needle or tip assembly according to the invention. The hollow needle is not shown in cross-section. The safety-shield is shown in an initial or nearly-fully extended position. This embodiment is similar to the second embodiment but additionally includes a system for locking the safety-shield in fully extended position and/or rendered the pen needle single-use;

FIG. 20 shows a rear end view of the pen needle or tip assembly of FIG. 18;

FIG. 21 shows a rear end view of the pen needle or tip assembly of FIG. 20 with the safety-shield removed;

FIG. 26 shows a side cross-section view of another non-limiting embodiment of a pen needle or tip assembly according to the invention. The hollow needle is not shown in cross-section. The safety-shield is shown in an initial or nearly-fully extended position. This embodiment is similar to the second embodiment but additionally includes a system for locking the safety-shield in fully extended position and/or rendered the pen needle single-use;

FIG. 27 shows a side view of the pen needle or tip assembly of FIG. 26;

FIGS. 33 and 34 show side cross-section and rear views of another non-limiting embodiment of a pen needle or tip assembly according to the invention. Like other embodiments, the embodiment utilizes a system for locking the safety-shield in a fully extended position so as to prevent re-use of the pen needle. This embodiment also illustrates how the pen needle can be individually packaged. The packaging includes a removable seal having a pull-tap and a removable front outer cover that extends to the seal—thereby completely enclosing the pen needle;

FIG. 45 shows a side cross-section view of another non-limiting embodiment of a pen needle or tip assembly according to the invention. The hollow needle is not shown in cross-section. This embodiment also utilizes a lockable safety-shield so as to prevent re-use of the pen needle and a removable front outer cover. The safety-shield is shown in an initial or nearly-fully extended position;

FIGS. 57 and 58 are rotated 90 degrees relative to FIGS. 55 and 56. The front cover can be removed and rotated 90 degrees and then reinstalled so that axial sliding on of the front cap causes the squeezing forces shown in FIG. 6.

DETAILED DESCRIPTION OF THE INVENTION

Figure 2:
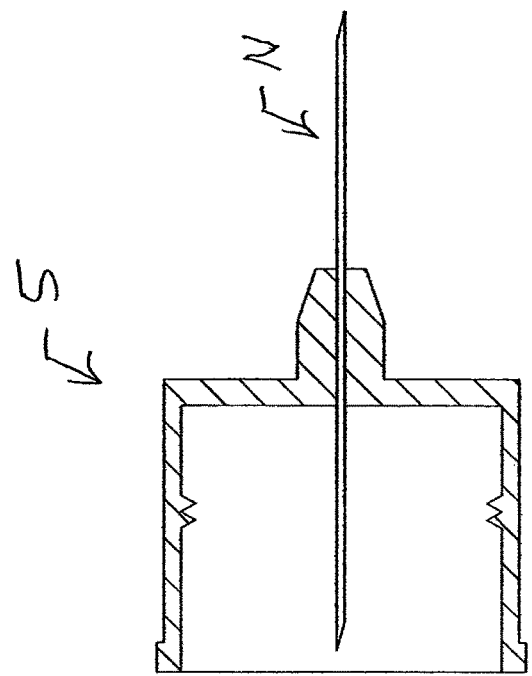
FIG. 2 shows a prior art needle tip assembly (in cross-section with the exception of the needle) in a position prior to installation onto the proximal end.
Figure 1:
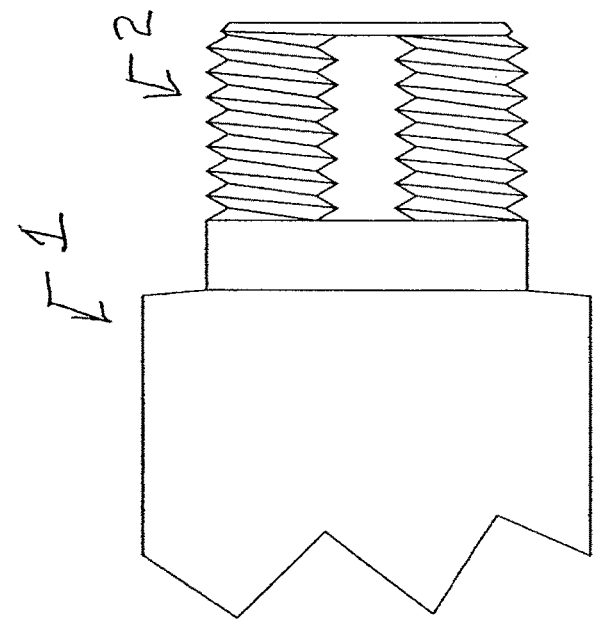
FIG. 1 shows an enlarged partial side view of a proximal end of a prior art pen needle device or pre-loaded syringe/injection device. The proximal end is shown with the cap removed and in a prior-use state, i.e., it is ready to receive thereon a needle tip or pen needle.
Figure 4:
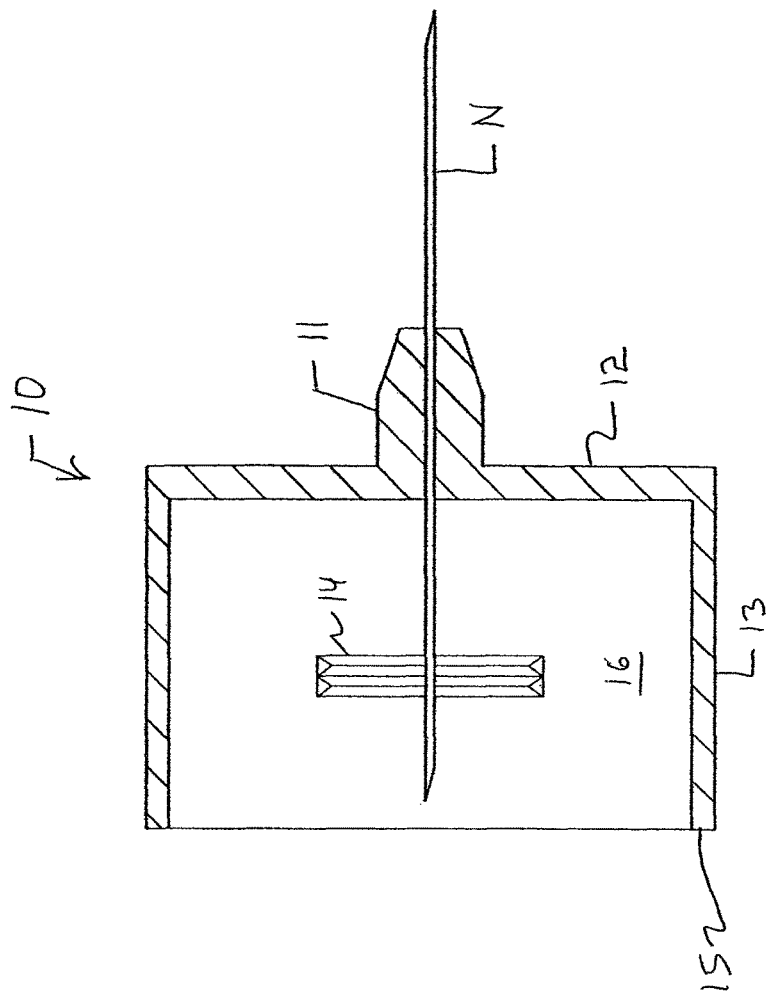
FIG. 4 shows a side cross-section view of the pen needle or tip assembly shown in FIG. 3. The hollow needle is not shown in cross-section.
Figure 3:
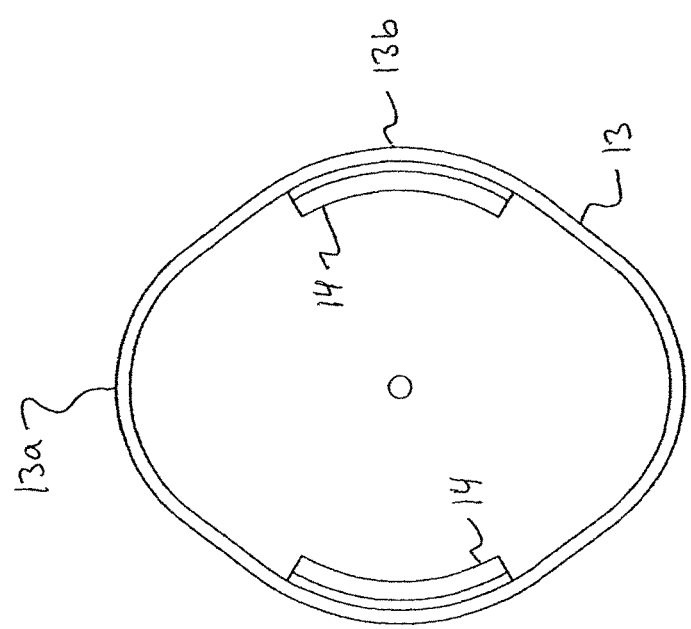
FIG. 3 shows a rear end view of a first non-limiting embodiment of a pen needle or tip assembly according to the invention.

Referring now to the drawings and first to FIGS. 3-6 which shows a first embodiment of a needle tip assembly. Although not shown, the needle tip assembly includes a needle tip cap (similar to cap 30 in US 2008/0154192) having various generally cylindrical portions with different diameters, a needle cap (similar to cap 40 in US 2008/0154192), and a pen needle or tip assembly 10. The proximal end of the pen needle 10 includes a needle N while the distal end 15 includes an opening which is sized to allow the pen needle 10 to be mounted to the threaded proximal end 2 of the pen needle injection device 1. The tip 10 includes a main support 11, a proximal surface, wall or end 12, an inner space 16, and two oppositely arranged thread sections 14. The body 13 has an generally oval shape, is made of an elastic material such as synthetic resin, and includes two oppositely arranged inwardly deformable/deflectable sections 13a and with two oppositely arranged outwardly deformable/deflectable sections 13b. Each thread section 14 is arranged on an internal surface of one of the two oppositely arranged outwardly deformable/deflectable sections 13b.

In accordance with one embodiment, in order to ensure that the pen needle 10 can be installed, removed and/or re-installed after use onto the proximal end 2, the pen needle 10 utilizes an oval body 13 which can be deformed from an initial or relaxed position (see FIG. 3) which allows the tip 10 to be threaded onto the section 2 and to a fully deformed position (see FIG. 6) which causes the thread sections 14 to expand radially and disengage from the threads of section 2, i.e., to deflect outwards by an amount which is sufficient to allow the tip 10 to be removed from (or installed onto) the proximal end 2.

In accordance with another optional embodiment, in order to ensure that the pen needle 10 is prevented from being re-installed after use onto the proximal end 2, the pen needle 10 utilizes an oval body 13 which can be deformed from an initial or relaxed position (see FIG. 3) to a slightly deformed position (not shown) which allows the tip 10 to be threaded onto the section 2, and to a fully deformed position (see FIG. 6) which causes the thread sections 14 to expand radially and disengage from the threads of section 2, i.e., to deflect outwards by an amount which is sufficient to allow the tip 10 to be removed from (or installed onto) the proximal end 2.

Figure 5:
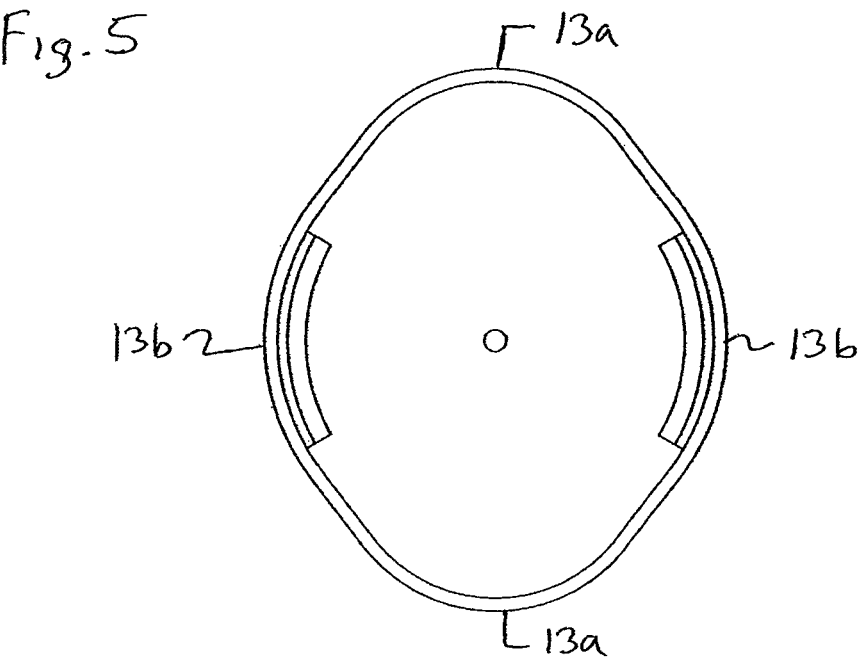
FIGS. 5 and 6 show rear end views of the pen needle or tip assembly of FIGS. 3 and 4 in an initial position (FIG. 5) and a compressed position (FIG. 6). The up and down facing arrows in FIG. 6 show how a squeezing force applied to deflectable sections of the body causes the sections of the body having the partial thread sections to move outwardly (as illustrated by the horizontal facing arrows)
Figure 6:
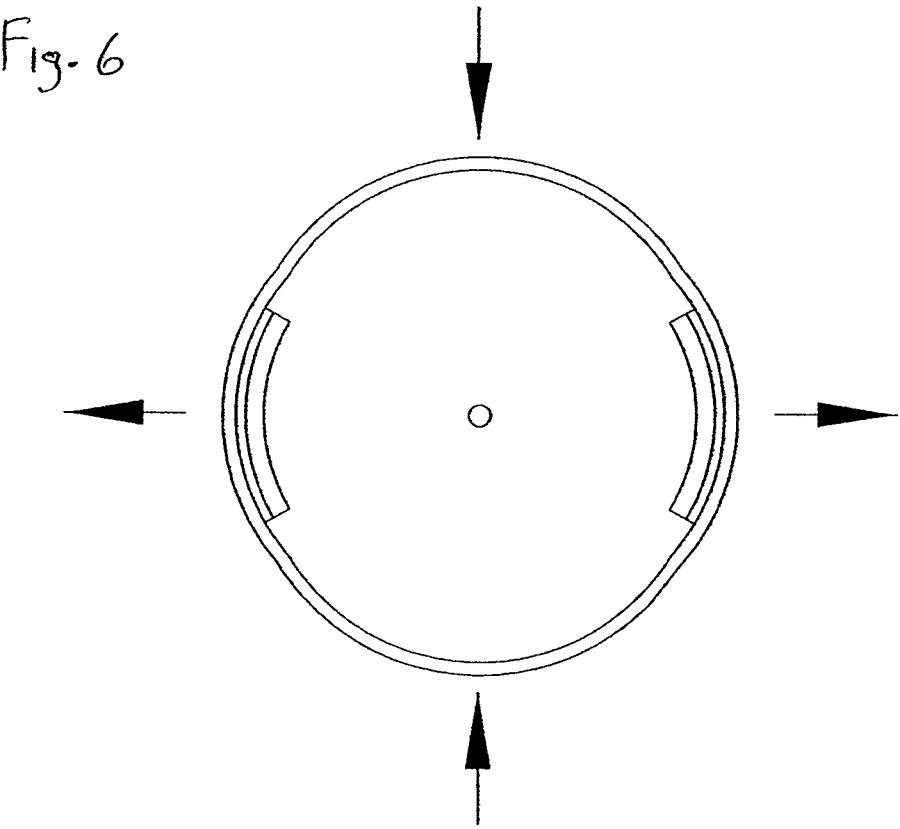

As can be seen in FIGS. 5 and 6, prior the needle tip assembly being installed onto the threaded proximal end 2, the user can grip the tip 10 (i.e., sections 13a of the tip 10) shown in FIG. 5 with his/her forefinger and thumb. Then, as shown in FIG. 6, he/she can squeeze sections 13a towards each other (indicated by vertical arrows) thereby causing outward radial deflection of sections 13b (indicated by horizontal arrows). In the position shown in FIG. 6, the user can then install the tip 10 onto the section 2 by axially moving it towards and over the section 2 until it assumes the installed position (see e.g., FIG. 6 of US 2008/0154192 or FIG. 11 of the instant application). Once the user releases the squeezing force indicated by vertical arrows in FIG. 6, the tip 10 will again substantially assume the shape shown in FIG. 5 owing to the elastic nature of the body 13.

Also with reference to FIGS. 5 and 6, if the needle tip assembly is already installed onto the threaded proximal end 2 (not shown in FIGS. 5 and 6), the user can grip the tip 10 (i.e., sections 13a of the tip 10) shown in FIG. 5 with his/her forefinger and thumb. Then, as shown in FIG. 6, he/she can squeeze sections 13a towards each other (indicated by vertical arrows) thereby causing outward radial deflection of sections 13b (indicated by horizontal arrows). In the position shown in FIG. 6, the user can then remove the tip 10 from the section 2 by axially moving it away from the section 2 and assumes the uninstalled position.

Also with reference to FIGS. 5 and 6, prior the needle tip assembly being installed onto the threaded proximal end 2, the user can grip the tip 10 (i.e., sections 13a of the tip 10) shown in FIG. 5 with his/her forefinger and thumb. Then, as shown in FIG. 6, he/she can squeeze sections 13a towards each other (indicated by vertical arrows) thereby causing outward radial deflection of sections 13b (indicated by horizontal arrows). In the position shown in FIG. 6, the user can then install the tip 10 onto the section 2 by axially moving it towards and over the section 2 until it assumes the installed position (see e.g., FIG. 6 of US 2008/0154192 or FIG. 11 of the instant application). After use in injection, the user can then remove the tip 10 by unthreading it from the section 2. This would occur by the user rotating the tip 10 until the sections 14 are fully unthreaded from the threads of the section 2.

Also with reference to FIGS. 5 and 6, prior the needle tip assembly being installed onto the threaded proximal end 2, the user can thread on the tip 10 (while in the relaxed position shown in FIG. 5) by rotating it onto section 2 until it is fully installed thereon. Then, as shown in FIG. 6, he/she can squeeze sections 13a towards each other (indicated by vertical arrows) thereby causing outward radial deflection of sections 13b (indicated by horizontal arrows). In the position shown in FIG. 6, the user can then remove the tip 10 from the section 2 by axially moving it away from the section 2 and then allow it to assume the relaxed position of FIG. 5.

The embodiment just described as well as those described below can be used in any of the non-limiting ways described above according to the invention.

FIGS. 7-17 show a second non-limiting embodiment of a pen needle or tip assembly according to the invention.

Corresponding features include the same reference numbers, but with an additional modifying symbol, e.g., feature 13' corresponds to feature 13. FIG. 8 shows a side cross-section view of the pen needle or tip 10' assembly which utilizes all of the features of the previous embodiment and additionally includes a safety-shield 20 and a spring S1 for biasing the shield 20 towards an extended position (see FIG. 9). The safety-shield 20 includes a generally circular front section 21 which (in the extended position) is sized and configured to extend out past the proximal end of the needle N and is configured to cover the needle N so that the user will be less likely to be pricked by the needle N. The safety-shield 20 also includes a generally circular through opening 22 which allows the needle N to pass there through when it is retracted (see FIG. 10). The safety-shield 20 further also includes plural, e.g., two oppositely arranged, generally partially circular legs 23 which connect the section 21 to distal projections 24. Each circular leg 23 is sized and configured to pass through and move within one of the partially circular slots 17' formed in the body 13' of the tip 10'. Each projection 24 is larger, i.e., thicker, than the slot 17' and is sized and configured to limit and define the axial movement/position of the safety-shield 20 in the fully extended position (see FIG. 9).

Figure 11:
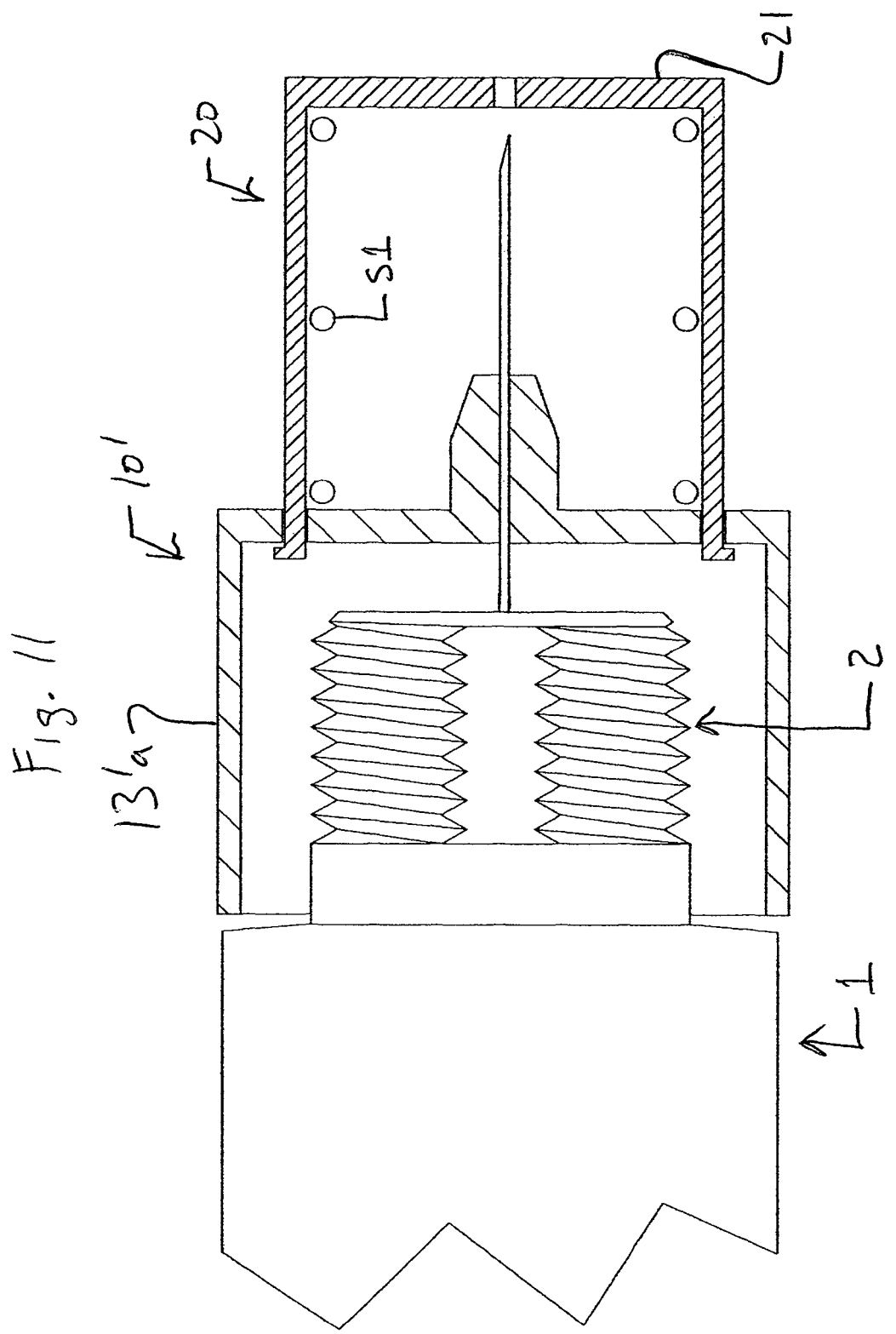
FIG. 11 shows a side cross-section view of the pen needle or tip assembly of FIGS. 7 and 8 installed on a prior art pen needle device or pre-loaded syringe/injection device. The safety-shield is in the initial or extended position.
Figure 17:
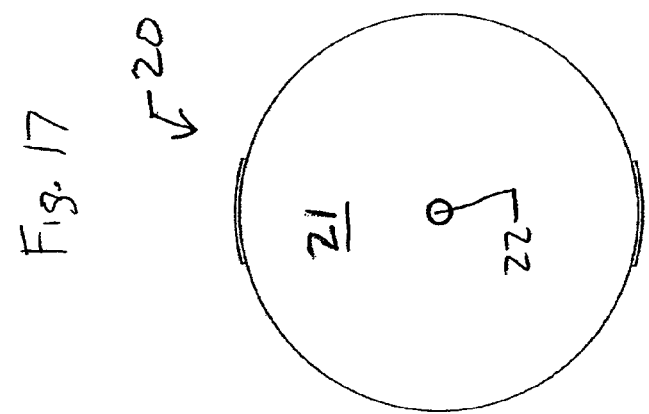
FIG. 17 shows a front end view of the safety-shield shown in FIG. 15.
Figure 15:
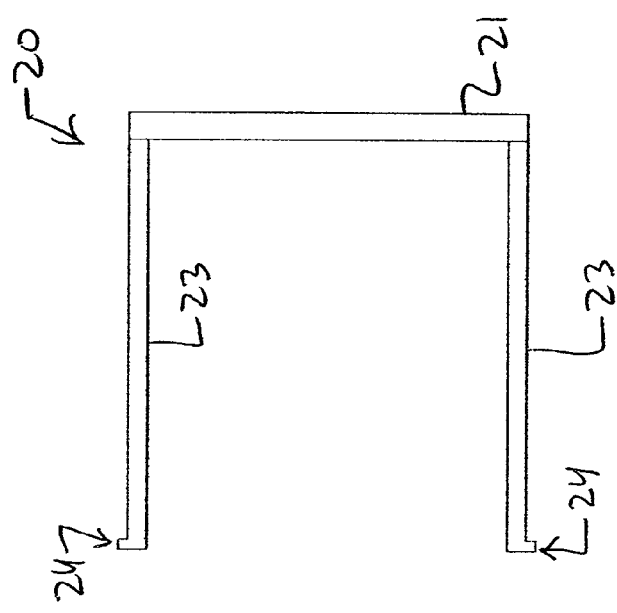
FIG. 15 shows a side view of the safety-shield that is used on the pen needle or tip assembly shown in FIGS. 7 and 8.
Figure 16:
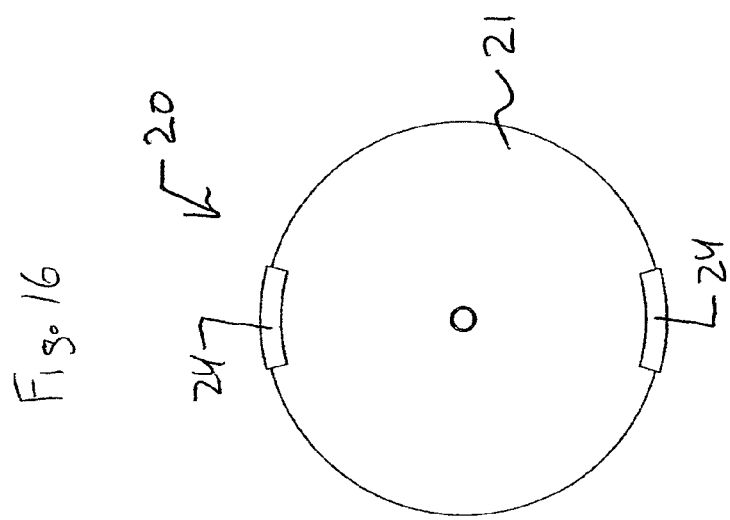
FIG. 16 shows a rear end view of the safety-shield shown in FIG. 15.
Figure 19:
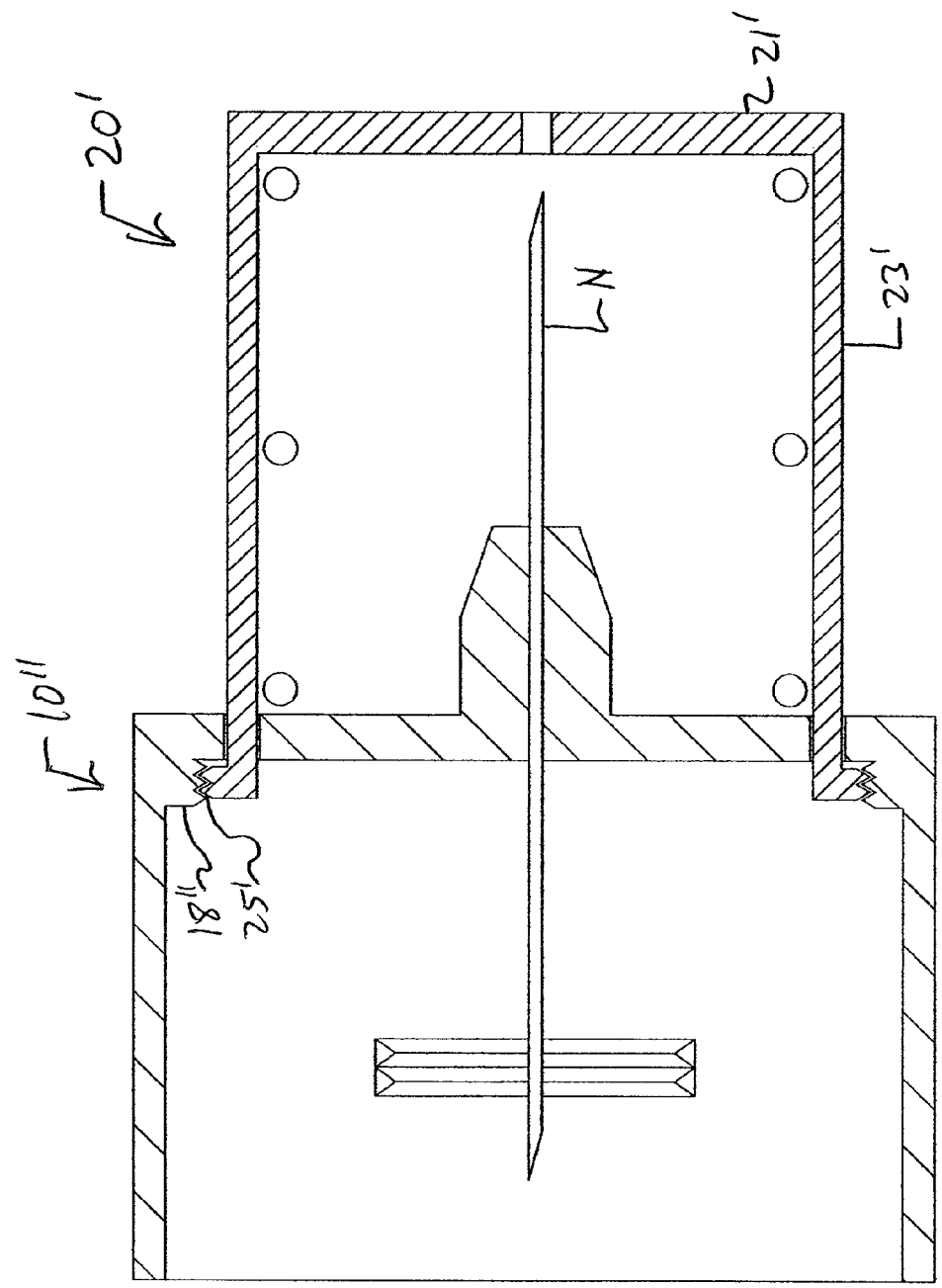
FIG. 19 shows a side cross-section view of the pen needle or tip assembly of FIG. 18 with the safety-shield being in a fully extended and locked position. In this position, the pen needle or tip assembly is rendered unreusable.

FIG. 11 shows how the pen needle or tip assembly 10' can be installed onto the threaded section 2 while the safety-shield 20 is in the extended position. This allows the user to more safely install the tip 10' without being pricked by the needle N which remains covered by the safety-shield 20. The tip 10' can be installed using any of the ways described above. By way of non-example, prior the needle tip assembly 10' being installed onto the threaded proximal end 2, the user can grip the tip 10' (i.e., sections 13'$a$ of the tip 10') with his/her forefinger and thumb. Then, in the same way as shown in FIG. 6, he/she can squeeze sections 13'$a$ towards each other (indicated by vertical arrows) thereby causing outward radial deflection of sections 13'$b$ (indicated by horizontal arrows in FIG. 6). In the squeezed position shown in FIG. 6, the user can then install the tip 10' onto the section 2 by axially moving it towards and over the section 2 until it assumes the installed position (FIG. 11). To use the device of FIG. 11, the user can move the device 1 so that the surface 21 contacts skin and then continue to apply sufficient force against the skin so that the safety-shield 20 retracts (FIG. 12) to expose the needle N and the needle N penetrates the skin by a sufficient or desired amount. After use in injection, the user can move the device 1 away from the skin which results in the safety-shield 20 moving automatically back to the extended position (FIG. 9) via the spring S1. After use, the user can then remove the tip 10' from the device 1 by, e.g., unthreading it from the section 2. This would occur by the user rotating the tip 10' until the sections 14' are fully unthreaded from the threads of the section 2. The user can alternatively remove the tip 10' from the device 1 by, e.g., squeezing sections 13'$a$ like the way shown in FIG. 6, and axially sliding the tip 10' away from and off of the section 2. Once removed, the tip 10' can be safely discarded as the safety-shield would reduce the likelihood of being pricked by the needle N when handling the tip 10'.

FIGS. 18-21 show another non-limiting embodiment of a pen needle or tip assembly according to the invention. Corresponding features include the same reference numbers, but with an additional modifying symbol, e.g., feature 13" corresponds to feature 13' or 13. FIG. 18 shows a side cross-section view of the pen needle or tip 10" assembly which utilizes all of the features of the previous embodiment including a safety-shield 20' and a spring S1 for biasing the shield 20' towards an extended position. The safety-shield 20' includes a generally circular front section 21' which (in the extended position) is sized and configured to extend out past the proximal end of the needle N and is configured to cover the needle N so that the user will be less likely to be pricked by the needle N. The safety-shield 20' also includes a generally circular through opening 22' which allows the needle N to pass there through when it is retracted. The safety-shield 20' further also includes plural, e.g., two oppositely arranged, generally partially circular legs 23' which connect the section 21' to distal projections 24'. Each circular leg 23' is sized and configured to pass through and move within one of the partially circular slots 17" formed in the body 13" of the tip 10". Each projection 24' is larger, i.e., thicker, than the slot 17" and is sized and configured to limit and define the axial movement/position of the safety-shield 20' in the fully extended and locked position (see FIG. 19). As is apparent from FIGS. 18 and 19, when each projection 24' is arranged just behind the locking sections 18" formed in the body 13", the safety-shield 20' in an initial and/or prior-use and nearly-fully extended position (see FIG. 18). However, when each projection 24' is engaged (owing to the external threads 25' engaging with the internal threads of sections 18") with the locking sections 18" formed in the body 13", the safety-shield 20' in a post-use of fully extended position (see FIG. 19). The locking engagement between threads 25' and the threads of each section 18" is such that once engaged, they become locked to each other and cannot disengaged from each other without essentially destroying or damaging the tip 10"—thereby rendering the tip 10" single-use.

The pen needle or tip assembly 10" shown in FIG. 18 can be installed onto the threaded section 2 while the safety-shield 20' is in the nearly-fully extended position. This allows the user to more safely install the tip 10" without being pricked by the needle N which remains covered by the safety-shield 20'. The tip 10" can be installed using any of the ways described above. By way of non-example, prior the needle tip assembly 10" being installed onto the threaded proximal end 2, the user can grip the tip 10" (i.e., sections 13"$a$ of the tip 10") with his/her forefinger and thumb. Then, in the same way as shown in FIG. 6, he/she can squeeze sections 13"$a$ towards each other (indicated by vertical arrows) thereby causing outward radial deflection of sections 13"$b$ (indicated by horizontal arrows in FIG. 6). In the squeezed position shown in FIG. 6, the user can then install the tip 10" onto the section 2 by axially moving it towards and over the section 2 until it assumes the installed position (not shown but similar to FIG. 11). To use the device 1 with the pen needle 10" installed thereon, the user can move the device 1 so that the surface 21' contacts skin and then continue to apply sufficient force against the skin so that the safety-shield 20' retracts to expose the needle N and the needle N penetrates the skin by a sufficient or desired amount. After use in injection, the user can move the device 1 away from the skin which results in the safety-shield 20' moving automatically back to the fully extended and locked position (FIG. 19) via the spring S1. After use, the user can then remove the tip 10" from the device 1 by, e.g., unthreading it from the section 2. This would occur by the user rotating the tip 10" until the sections 14" are fully unthreaded from the threads of the section 2. The user can alternatively remove the tip 10" from the device 1 by, e.g., squeezing sections 13"$a$ like the way shown in FIG. 6, and axially sliding the tip 10" away from and off of the section 2. Once removed, the tip 10" can be safely discarded as the safety-shield 20' would reduce the likelihood of being pricked by the needle N when handling the tip 10".

Figure 22:
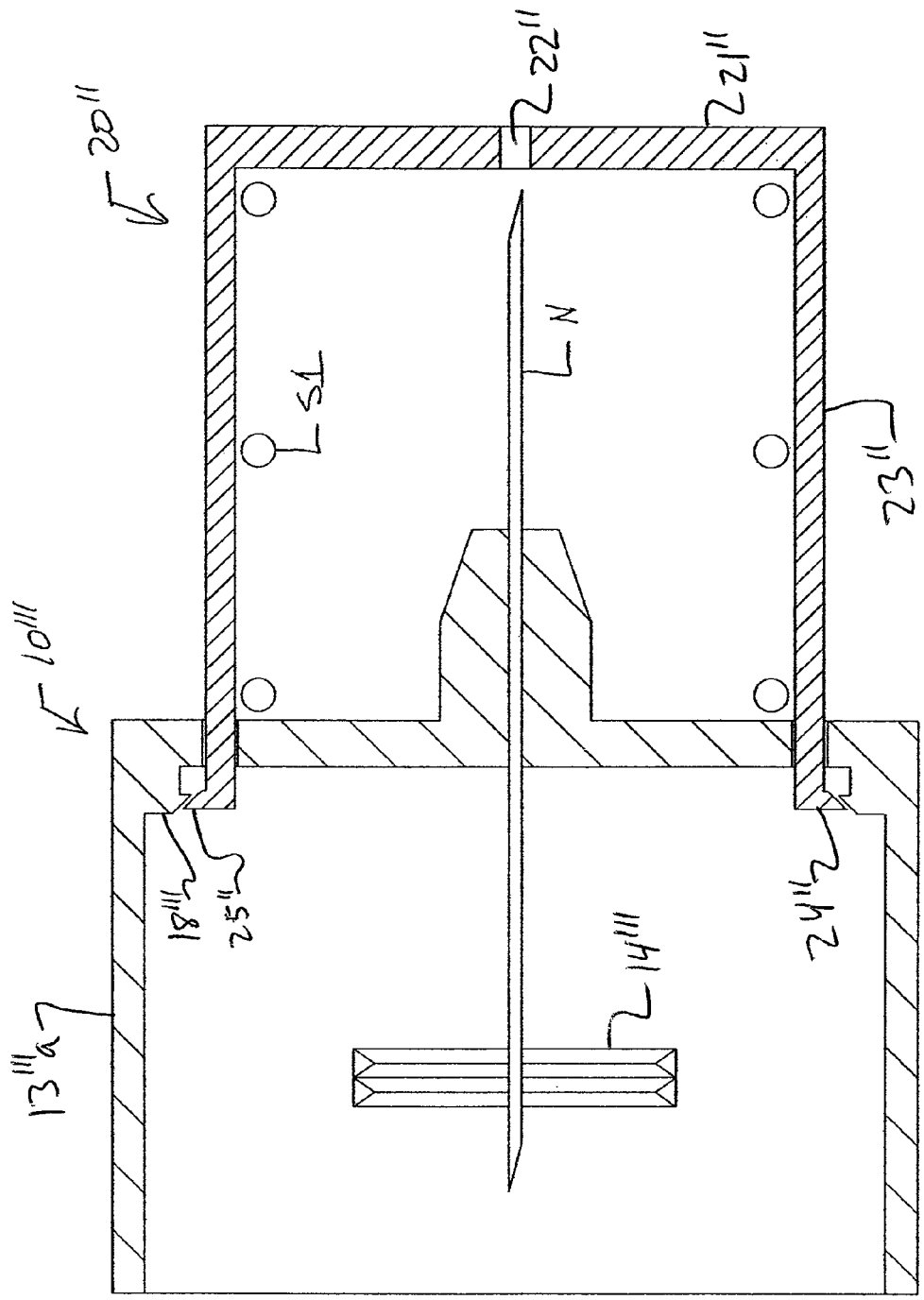
FIG. 22 shows a side cross-section view of another non-limiting embodiment of a pen needle or tip assembly according to the invention. The hollow needle is not shown in cross-section. The safety-shield is shown in an initial or nearly-fully extended position. This embodiment is similar to the second embodiment but additionally includes a system for locking the safety-shield in fully extended position and/or rendered the pen needle single-use.
Figure 23:
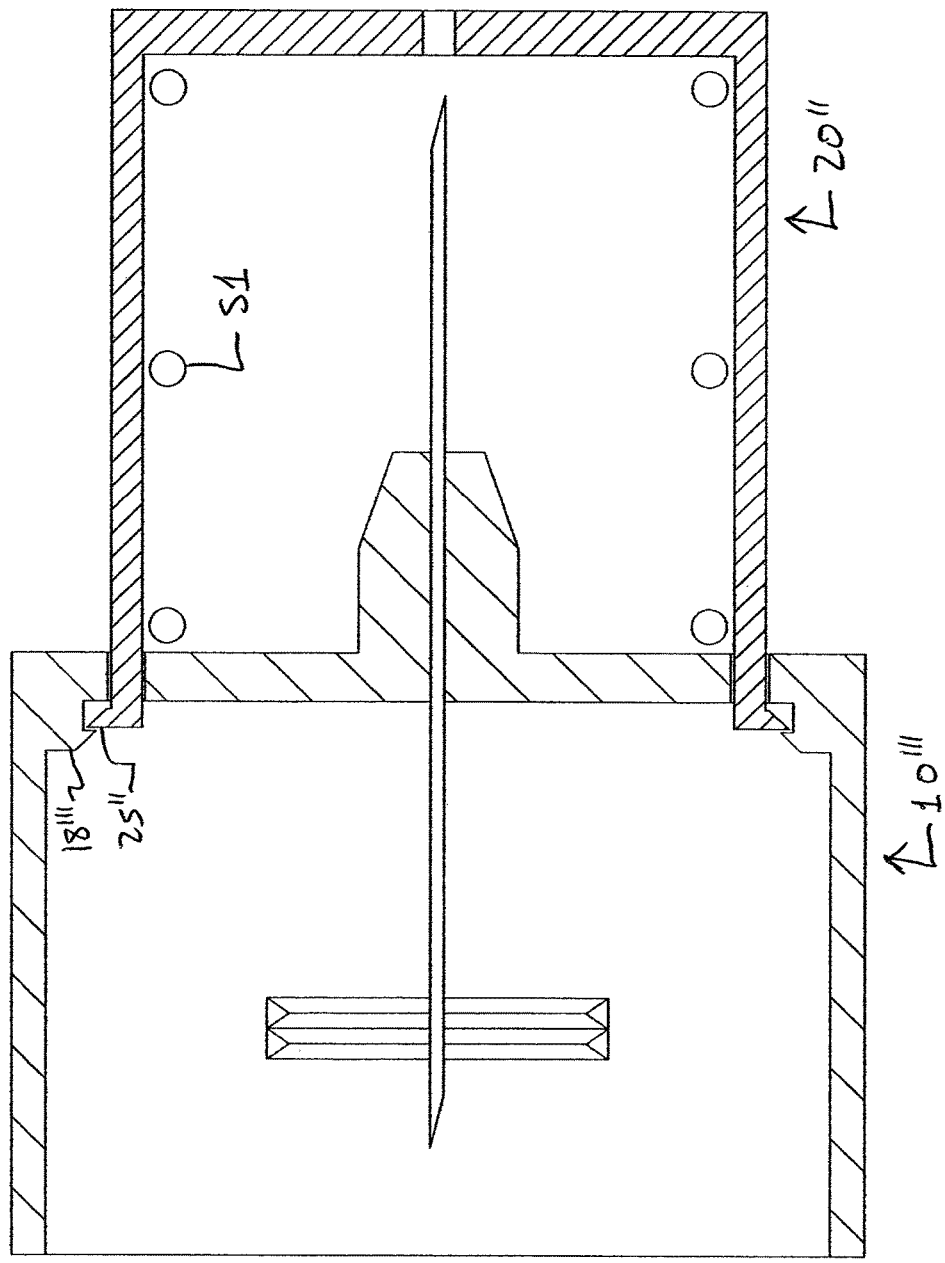
FIG. 23 shows a side cross-section view of the pen needle or tip assembly of FIG. 22 with the safety-shield being in a fully extended and locked position. In this position, the pen needle or tip assembly is rendered unreusable.

FIGS. 22 and 23 show another non-limiting embodiment of a pen needle or tip assembly according to the invention. Corresponding features include the same reference numbers, but with an additional modifying symbol, e.g., feature 13''' corresponds to feature 13" or 13' or 13. FIG. 22 shows a side cross-section view of the pen needle or tip 10''' assembly which utilizes all of the features of the previous embodiment including a safety-shield 20" and a spring S1 for biasing the shield 20" towards an extended position. The safety-shield 20" includes a generally circular front section 21" which (in the extended position) is sized and configured to extend out past the proximal end of the needle N and is configured to cover the needle N so that the user will be less likely to be pricked by the needle N. The safety-shield 20" also includes a generally circular through opening 22" which allows the needle N to pass there through when it is retracted. The safety-shield 20" further also includes plural, e.g., two oppositely arranged, generally partially circular legs 23" which connect the section 21" to distal projections 24". Each circular leg 23" is sized and configured to pass through and move within one of the partially circular slots 17''' formed in the body 13''' of the tip 10'''. Each projection 24" is larger, i.e., thicker, than the slot 17''' and is sized and configured to limit and define the axial movement/position of the safety-shield 20" in the fully extended and locked position (see FIG. 23). As is apparent from FIGS. 22 and 23, when each projection 24" is arranged just behind the locking sections 18''' formed in the body 13''', the safety-shield 20" in an initial and/or prior-use and nearly-fully extended position (see FIG. 22). However, when each projection 24" is engaged (owing to the external tapered projection 25" engaging with the internal tapered locking projection of sections 18''') with the locking sections 18''' formed in the body 13''', the safety-shield 20" in a post-use of fully extended position (see FIG. 23). The locking engagement between the projection 25" and the projection of each sections 18''' is such that once engaged (FIG. 23), they become locked to each other and cannot disengaged from each other without essentially destroying or damaging the tip 10'''—thereby rendering the tip 10''' single-use.

The pen needle or tip assembly 10''' shown in FIG. 22 can be installed onto the threaded section 2 while the safety-shield 20" is in the nearly-fully extended position. This allows the user to more safely install the tip 10''' without being pricked by the needle N which remains covered by the safety-shield 20". The tip 10''' can be installed using any of the ways described above. By way of non-example, prior the needle tip assembly 10''' being installed onto the threaded proximal end 2, the user can grip the tip 10''' (i.e., sections 13'''a of the tip 10''') with his/her forefinger and thumb. Then, in the same way as shown in FIG. 6, he/she can squeeze sections 13'''a towards each other (indicated by vertical arrows) thereby causing outward radial deflection of sections 13'''b (indicated by horizontal arrows in FIG. 6). In the squeezed position shown in FIG. 6, the user can then install the tip 10''' onto the section 2 by axially moving it towards and over the section 2 until it assumes the installed position (not shown but similar to FIG. 11). To use the device 1 with the pen needle 10''' installed thereon, the user can move the device 1 so that the surface 21" contacts skin and then continue to apply sufficient force against the skin so that the safety-shield 20" retracts to expose the needle N and the needle N penetrates the skin by a sufficient or desired amount. After use in injection, the user can move the device 1 away from the skin which results in the safety-shield 20" moving automatically back to the fully extended and locked position (FIG. 23) via the spring S1. After use, the user can then remove the tip 10''' from the device 1 by, e.g., unthreading it from the section 2. This would occur by the user rotating the tip 10''' until the sections 14''' are fully unthreaded from the threads of the section 2. The user can alternatively remove the tip 10''' from the device 1 by, e.g., squeezing sections 13'''a like the way shown in FIG. 6, and axially sliding the tip 10''' away from and off of the section 2. Once removed, the tip 10''' can be safely discarded as the safety-shield 20" would reduce the likelihood of being pricked by the needle N when handling the tip 10'''.

Figure 24:
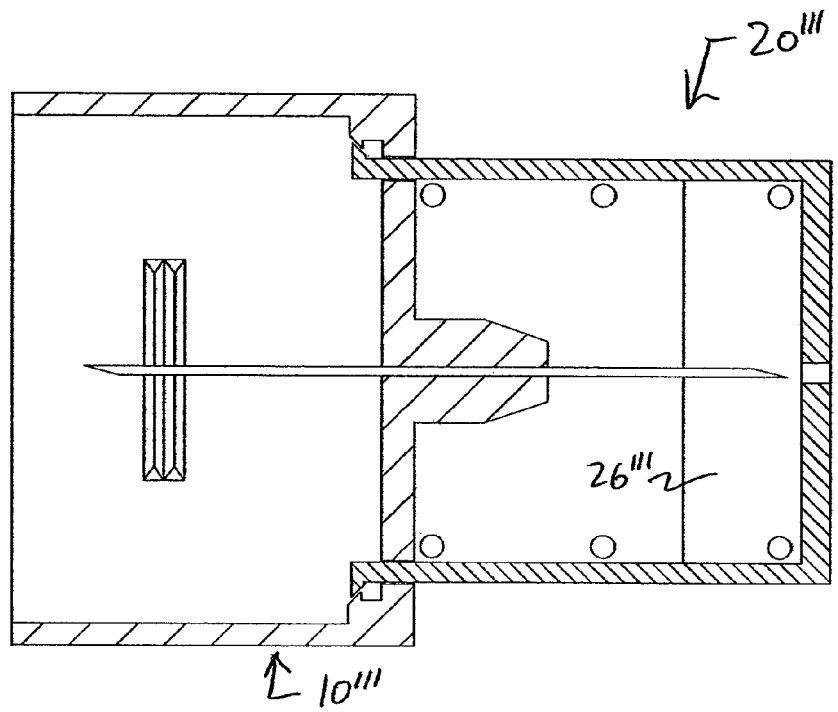
FIG. 24 shows a side cross-section view of another non-limiting embodiment of a pen needle or tip assembly according to the invention. The hollow needle is not shown in cross-section. The safety-shield is shown in an initial or nearly-fully extended position. This embodiment is similar to the second embodiment but additionally includes a system for locking the safety-shield in fully extended position and/or rendered the pen needle single-use.
Figure 25:
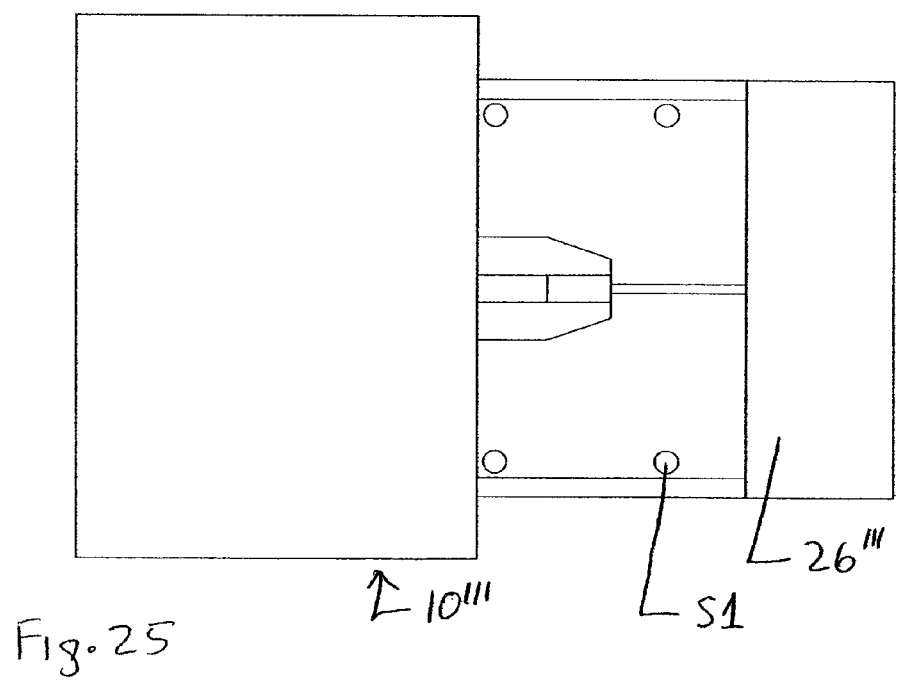
FIG. 25 shows a side view of the pen needle or tip assembly of FIG. 24.

FIGS. 24 and 25 show another non-limiting embodiment of a pen needle or tip assembly according to the invention. This embodiment is similar to the previous embodiment but additionally includes a surrounding circumferential wall 26''' on the safety-shield 20'''. The wall 26''' provides stiffening to the safety-shield, functions to more securely retain the spring S1, and also provides an additional level of protection for the puncturing end of the needle N thereby ensuring that the safety-shield 20''' cannot be deflected sideways to the point where the needle N is exposed. This modification can be utilized on any of the herein disclosed embodiments using a safety-shield to the extent desirable.

FIGS. 26 and 27 show another non-limiting embodiment of a pen needle or tip assembly according to the invention. This embodiment is also similar to the embodiment of FIGS. 22 and 23 but additionally includes spring retaining projections 27$^{IV}$ and a surrounding circumferential flange 19$^{IV}$ on the body of the tip 10$^{IV}$. The flange 19$^{IV}$ and projections 27$^{IV}$ function to more securely retain the spring S1. This modification can be utilized on any of the herein disclosed embodiments using a safety-shield to the extent desirable.

Figure 28:
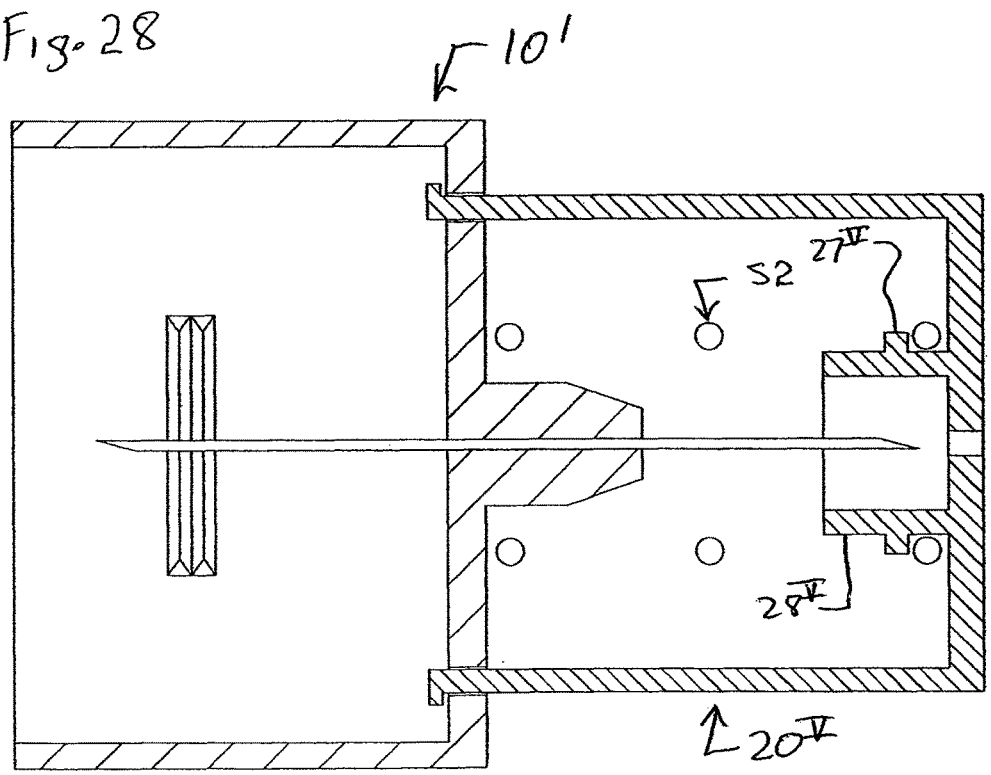
FIG. 28 shows a side cross-section view of another non-limiting embodiment of a pen needle or tip assembly according to the invention. The hollow needle is not shown in cross-section. The safety-shield is shown in an initial or fully extended position.
Figure 29:
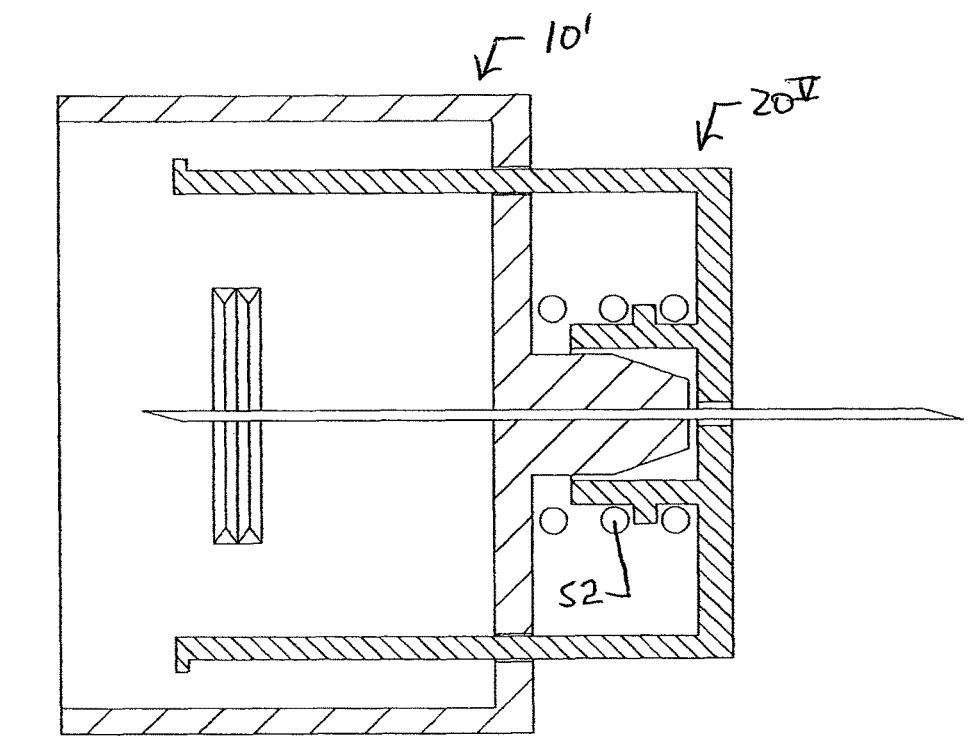
FIG. 29 shows a side cross-section view of the pen needle or tip assembly of FIG. 28. The safety-shield is shown in a using/injection or fully retracted position.

FIGS. 28 and 29 show another non-limiting embodiment of a pen needle or tip assembly according to the invention. This embodiment is similar to the embodiment of FIGS. 7-17 except that it utilizes a smaller diameter spring S2 and additionally includes spring retaining projections 27$^{V}$ arranged on a surrounding circumferential flange 28$^{V}$ on the safety-shield 20$^{V}$. The flange 28$^{V}$ and projection 28$^{V}$ function to more securely retain the spring S2 and also provides an additional level of protection for the puncturing end of the needle N thereby ensuring that the safety-shield 20$^{V}$ cannot be deflected sideways to the point where the needle N is exposed. This modification can be utilized on any of the herein disclosed embodiments using a safety-shield to the extent desirable.

Figure 30:
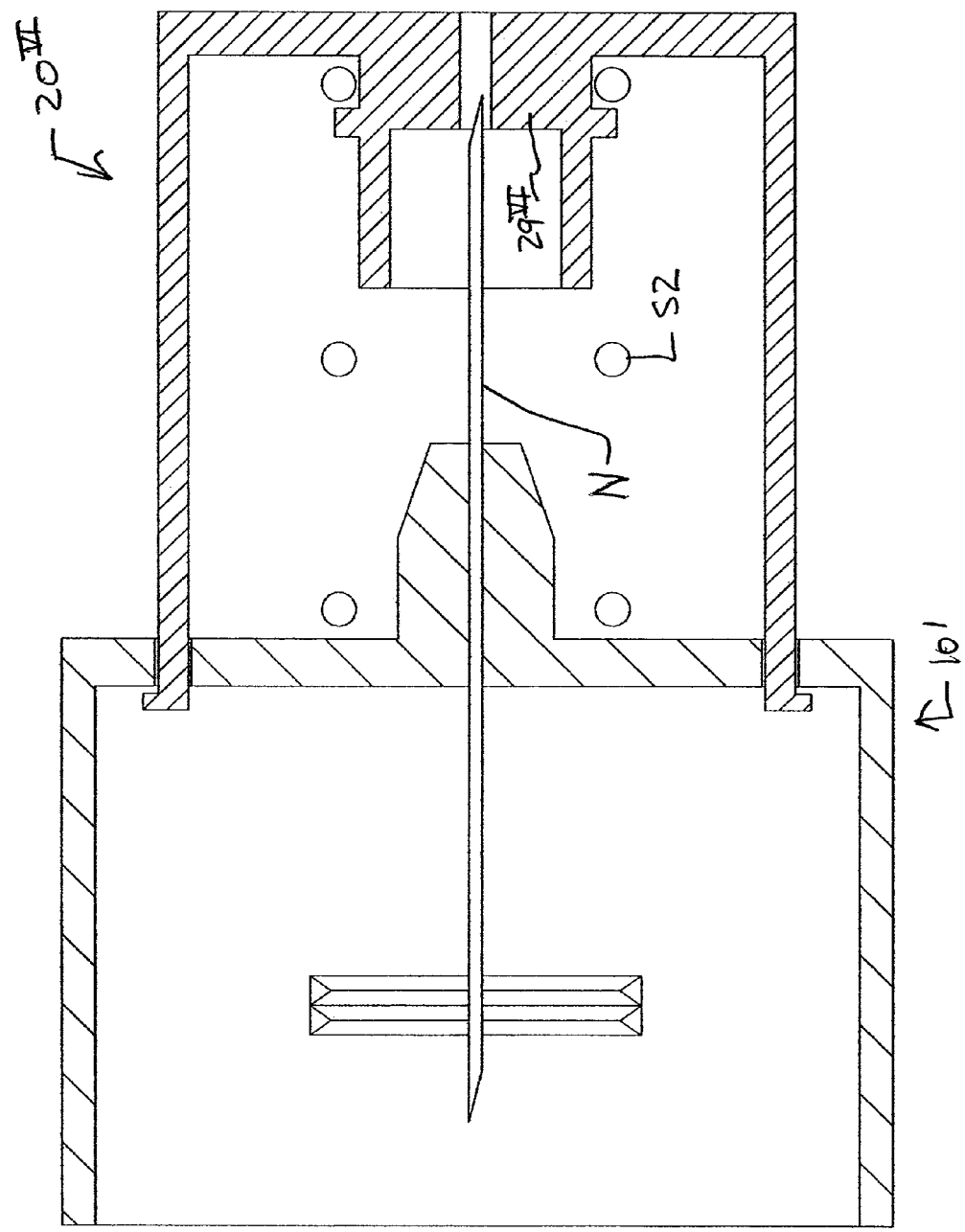
FIG. 30 shows a side cross-section view of another non-limiting embodiment of a pen needle or tip assembly according to the invention. The hollow needle is not shown in cross-section. The safety-shield is shown in an initial or fully extended position.

FIG. 30 shows another non-limiting embodiment of a pen needle or tip assembly according to the invention. This embodiment is similar to the embodiment of FIGS. 28 and 29 except that it utilizes an axially thicker surrounding circumferential flange 28$^{VI}$ on the safety-shield 20$^{VI}$. The flange 28$^{VI}$ and projection arranged thereon function to more securely retain the spring S2 and also provides an additional level of protection for the puncturing end of the needle N thereby ensuring that the safety-shield 20$^{VI}$ cannot be deflected sideways to the point where the needle N is exposed. This modification can be utilized on any of the herein disclosed embodiments using a safety-shield to the extent desirable.

Figure 31:
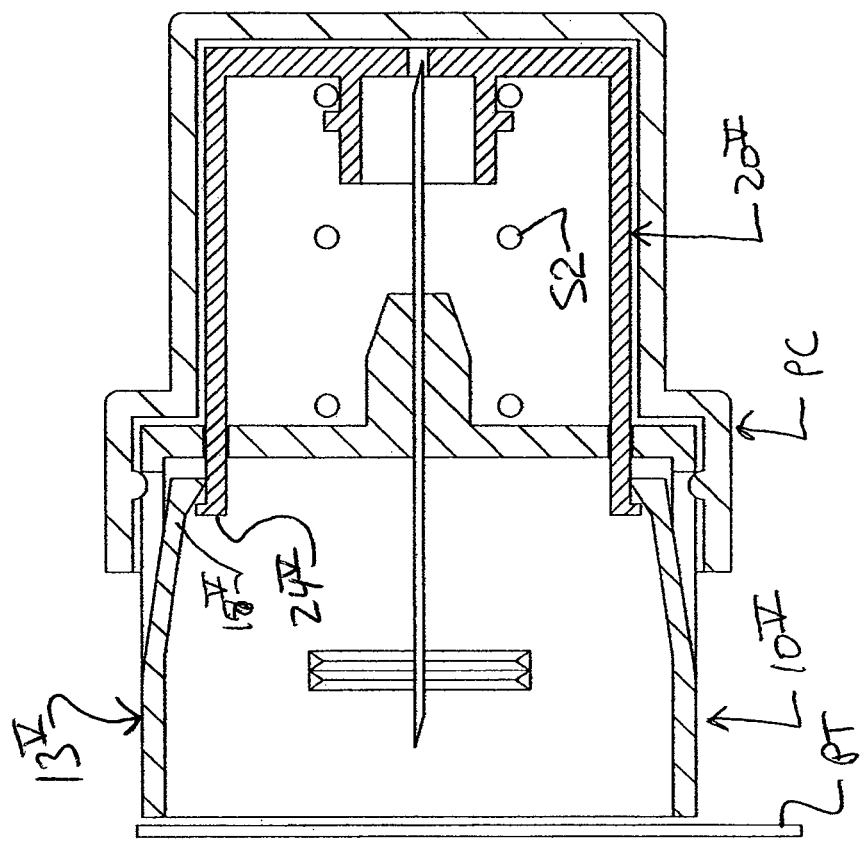
FIGS. 31 and 32 show side cross-section and rear views of another non-limiting embodiment of a pen needle or tip assembly according to the invention. Like other embodiments, the embodiment utilizes a system for locking the safety-shield in a fully extended position so as to prevent re-use of the pen needle. This embodiment also illustrates how the pen needle can be individually packaged. The packaging includes a removable seal having a pull-tap and a removable front outer cover.
Figure 32:
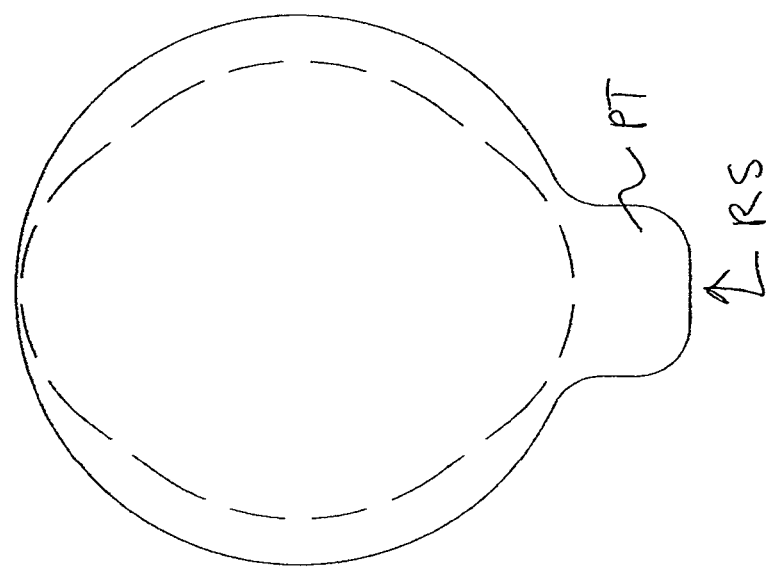

FIGS. 31 and 32 show another non-limiting embodiment of a pen needle or tip assembly according to the invention. Like other embodiments, the embodiment utilizes a system 18$^{V}$/24$^{V}$ for locking the safety-shield 20$^{V}$ in a fully extended position so as to prevent re-use of the pen needle 10$^{V}$. This embodiment also illustrates how the pen needle 10$^{V}$ can be individually packaged. The packaging includes a removable seal RS having a pull-tap PT and a removable front or protective or outer cover PC. The removable seal RS can be a material of the type used conventionally in packaging pen needles except that it is removably adhesively attached to the distal edge of the pen needle body $13^V$. The cover PC has a mechanism, e.g., projections, that allows the cover PC to be releasably retained on the tip $10^V$ while protecting the safety-shield $20^V$ and ensuring that the safety-shield $20^V$ is not accidentally moved to the retracted position. In order to use the packaged pen needle $10^V$ shown in FIGS. 31 and 32, the user need only remove the removable seal RS by gripping the pull-tab PT and peeling it off of the body $13^V$. The user can then install the pen needle $10^V$ onto the section 2 in any manner described herein. Then, the user can remove the protective cover PC and use the pen needle $10^V$ for injection. The user can then re-install the protective cover PC and then remove the pen needle $10^V$ from the section 2. However, this is not necessary if the safety-shield $20^V$ is in the fully extended position (see FIG. 36) because deflectable members $18^V$ will be positioned behind members $24^V$ and prevent distal movement of the safety-shield $20^V$. Instead, the user can simply remove the pen needle $10^V$ from the section 2 without the protective cover PC being installed thereon. The packaging system PC/RS of this embodiment can be utilized on any of the herein disclosed embodiments, especially those using a safety-shield, to the extent desirable.

FIGS. 33 and 34 show another non-limiting embodiment of a pen needle or tip assembly according to the invention. This embodiment is similar to that of FIGS. 31 and 32 except that it utilizes a removable front outer cover PC' that extends to the seal RS (with the seal RS being adhesively attached to a distal edge of the cover PC')—thereby completely enclosing the pen needle $10^V$. The packaging thus includes a removable seal RS having a pull-tap PT and a removable front or protective or outer cover PC'. The removable seal RS can be a material of the type used conventionally in packaging pen needles except that it is removably adhesively attached to the distal edge of the pen needle body $13^V$. The cover PC' may optionally utilize a mechanism, e.g., projections, (not shown) that allows the cover PC' to be releasably retained on the tip $10^V$ while protecting the safety-shield $20^V$ and ensuring that the safety-shield $20^V$ is not accidentally moved to the retracted position. In order to use the packaged pen needle $10^V$ shown in FIGS. 33 and 34, the user need only remove the removable seal RS by gripping the pull-tab PT and peeling it off of the cover PC'. Then, the user can remove the protective cover PC and use the pen needle $10^V$ for injection. After use, the safety-shield $20^V$ will be in the fully extended position (see FIG. 36) because deflectable members $18^V$ will be positioned behind members $24^V$ and prevent distal movement of the safety-shield $20^V$. The user can thus simply remove the pen needle $10^V$ from the section 2 without the protective cover PC' being installed thereon. The packaging system PC'/RS of this embodiment can be utilized on any of the herein disclosed embodiments, especially those using a safety-shield, to the extent desirable.

Figure 35:
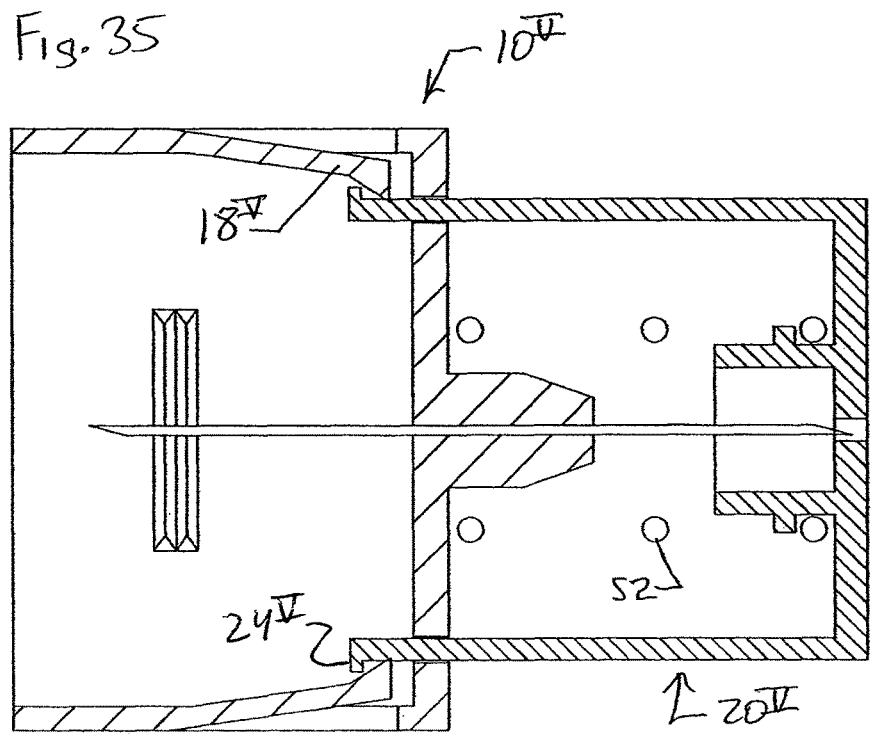
FIG. 35 shows a side cross-section view of the pen needle used in the embodiments of FIGS. 31-34 with the packaging removed. The hollow needle is not shown in cross-section. The safety-shield is shown in an initial or nearly-fully extended position.
Figure 36:
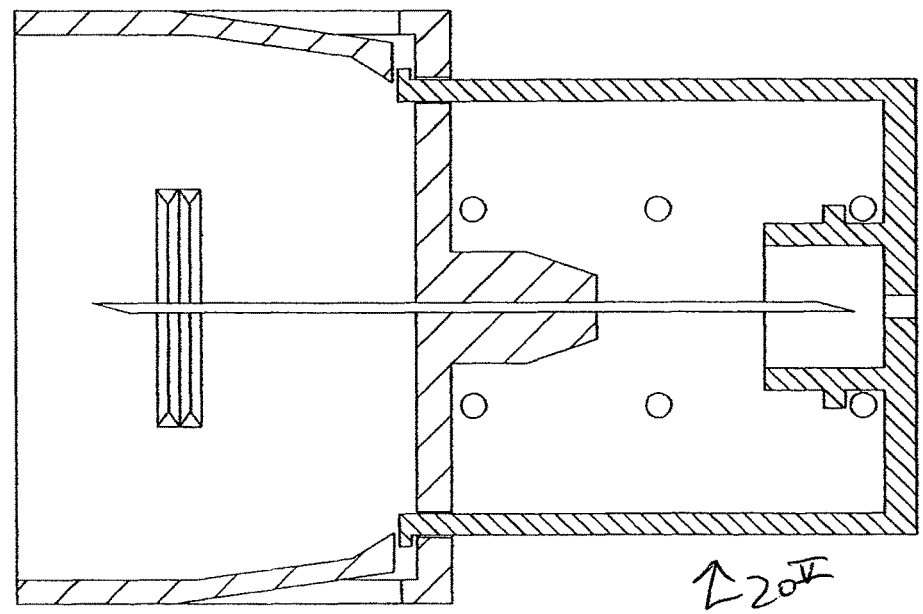
FIG. 36 shows a side cross-section view of the pen needle or tip assembly of FIG. 35 with the safety-shield being in a fully extended and locked position. In this position, the pen needle or tip assembly is rendered unreusable.
Figure 37:
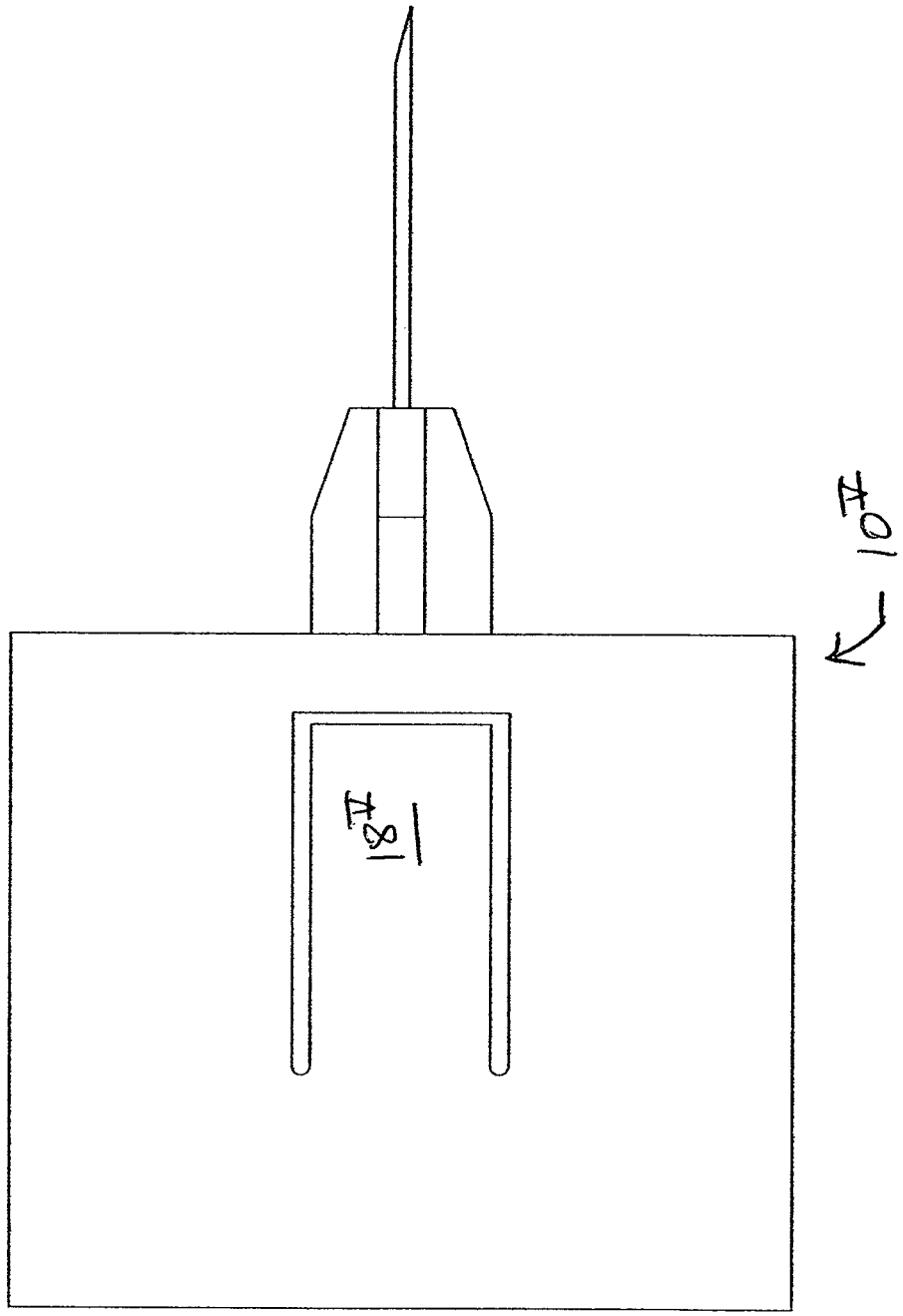
FIG. 37 shows a side view of the pen needle or tip assembly of FIGS. 35 and 36 with the safety-shield removed and rotated 90 degrees.
Figure 38:
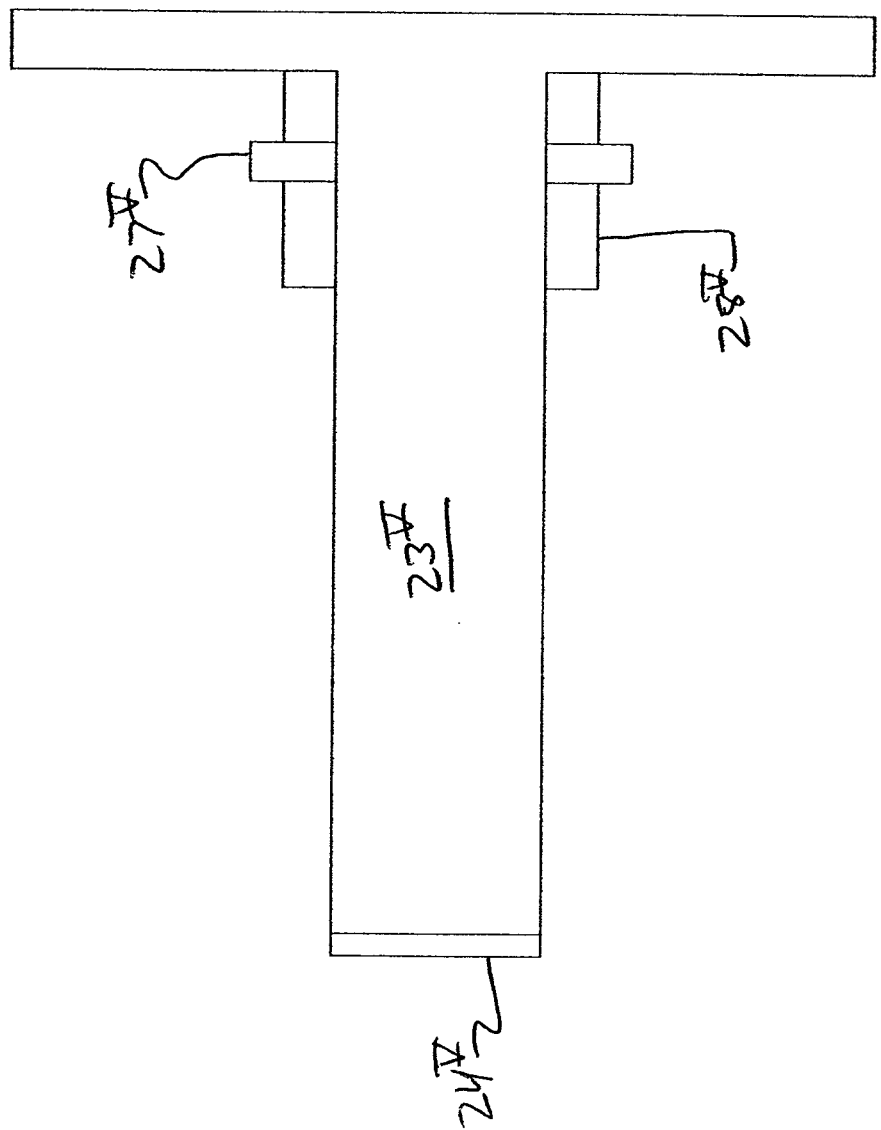
FIG. 38 shows a side view of the safety-shield used in the assembly of FIGS. 35 and 36 and rotated 90 degrees.
Figure 39:
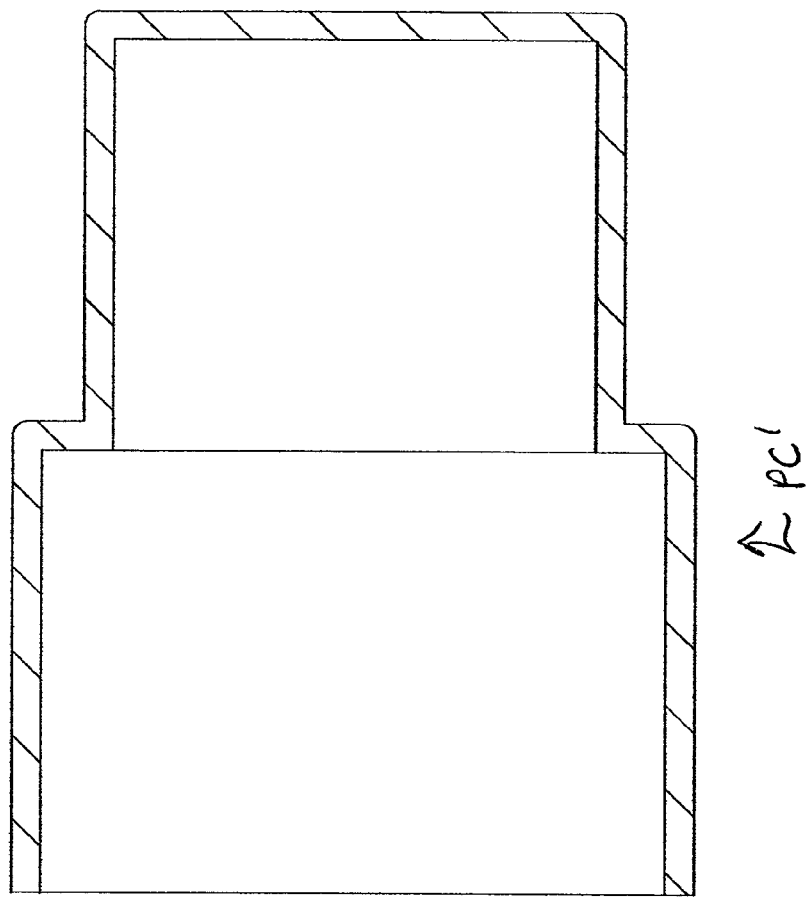
FIG. 39 shows a side cross-section view of the front cover used in the embodiment shown in FIG. 33.
Figure 40:
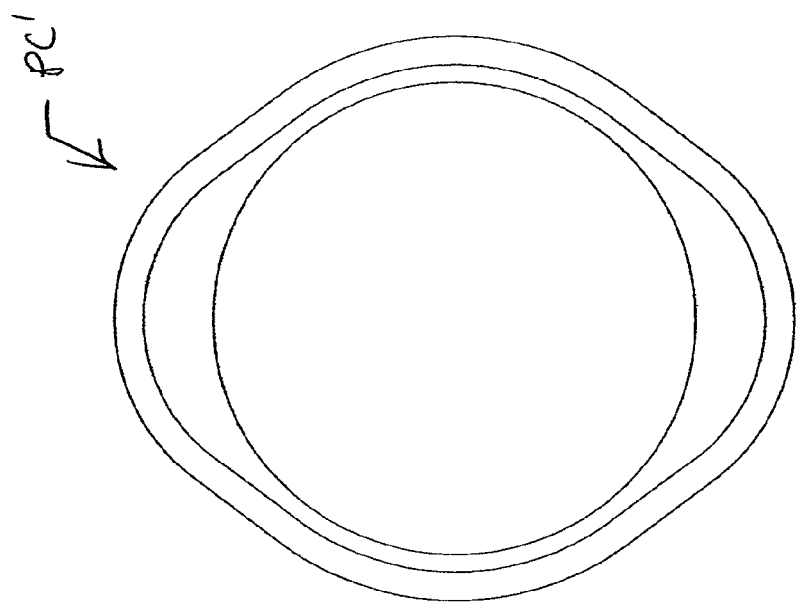
FIG. 40 shows a rear view of the front cover shown in FIG. 39.

FIGS. 35 and 36 show the pen needle $10^V$ used in the embodiments of FIGS. 31-34 with the packaging removed. The hollow needle is not shown in cross-section. In FIG. 35, the safety-shield $20^V$ is shown in an initial or nearly-fully extended position. In FIG. 36, the safety-shield $20^V$ is in a fully extended and locked position. In this position, the pen needle or tip assembly $10^V$ is rendered unreusable and can be safely handled and discarded. The safety-shield $20^V$ moves to the position shown in FIG. 36 automatically under the action of the spring S2 once the force retaining the safety-shield $20^V$ in the retracted position (as occurs during injection) is removed. The spring S2 produces an expansion force sufficient to allow portions $24^V$ to cause outward deflection of the deflectable members $18^V$ and move to a position in front of the same. Once in front, the members $18^V$ move back to an original position inwardly deflected position shown in FIG. 36. As can be seen in FIG. 37, each of the two oppositely arranged members $18^V$ are integrally formed with the body of the tip $10^V$. As can be seen in FIG. 38, the safety-shield $20^V$ is a one-piece integrally formed member. Furthermore, as can be seen in FIG. 40, the cover PC' is a one-piece integrally formed member.

Figure 41:
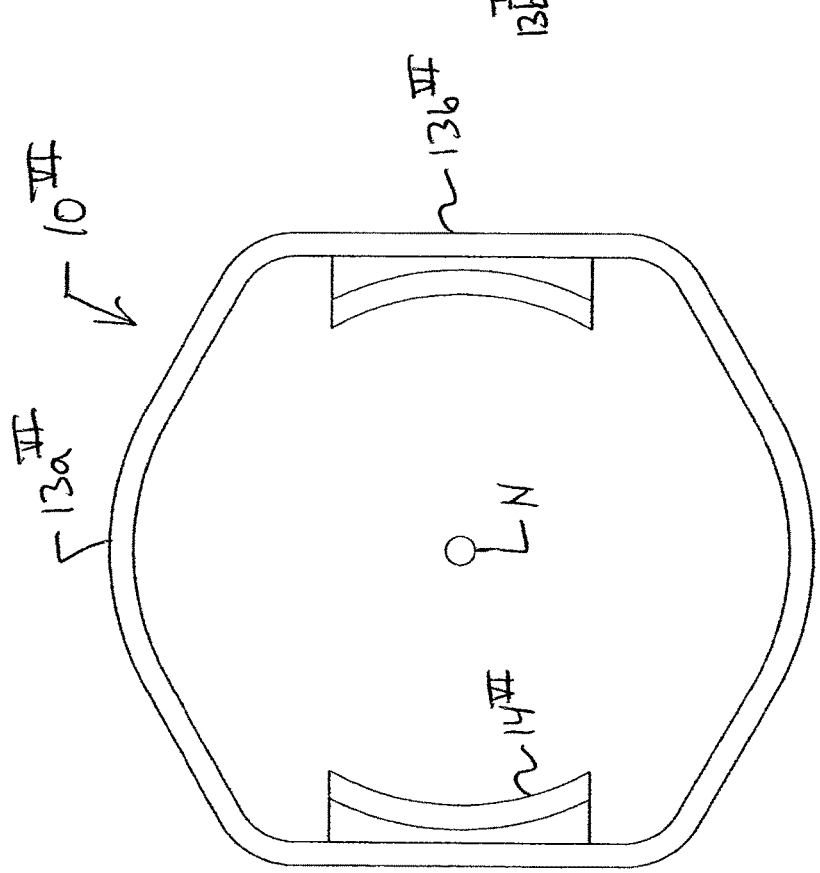
FIG. 41 shows a rear end view of another non-limiting embodiment of a pen needle or tip assembly according to the invention. In this embodiment, the pen needle body is more rectangular-shaped than the oval-shape shown in FIG. 3.

FIG. 41 shows a rear end view of another non-limiting embodiment of a pen needle or tip assembly according to the invention. In this embodiment, the body of the pen needle $10^{VI}$ is more rectangular-shaped than the oval-shape shown in FIG. 3. As with previous embodiments, the body utilizes sections $13a^{VI}$ which can be gripped by a user and squeezed together to cause the sections $13b^{VI}$ to expand radially outwardly and thereby cause the thread sections $14^{VI}$ to disengage from the threads of the section 2. The embodiment shown in FIG. 41 does not utilize a safety-shield.

Figure 42:
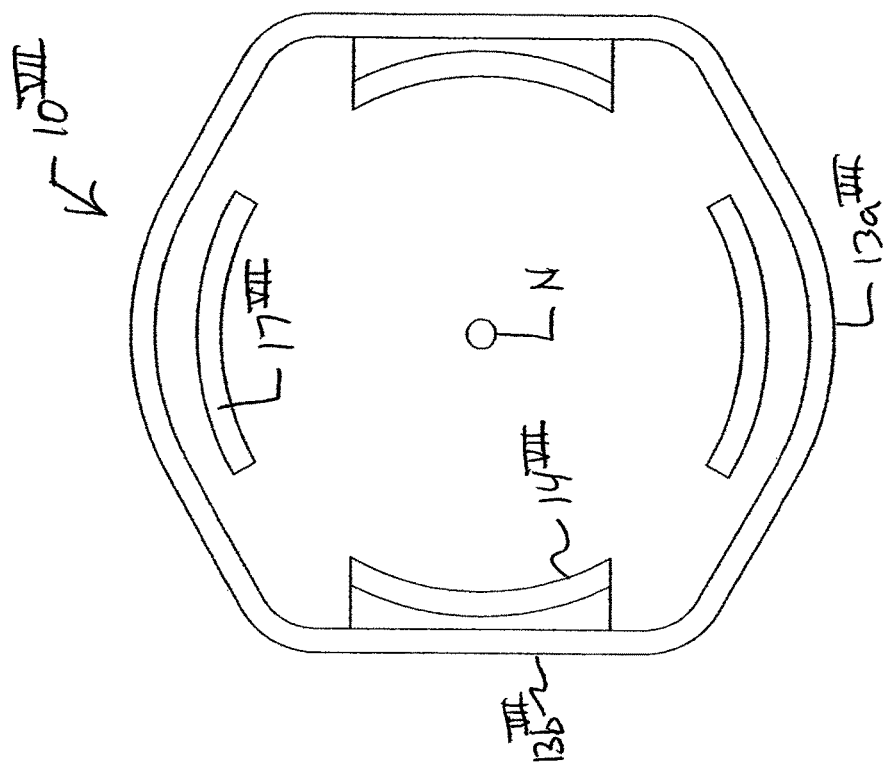
FIG. 42 shows a rear end view of another non-limiting embodiment of a pen needle or tip assembly according to the invention. In this embodiment, the pen needle body shown in FIG. 41 is modified to utilize a needle-shield (not shown) and utilizes slots that receive therein portions of the safety-shield.

FIG. 42 shows a rear end view of another non-limiting embodiment of a pen needle or tip assembly according to the invention. In this embodiment, the body of the pen needle $10^{VII}$ is similar to that shown in FIG. 41 except that it utilizes a safety-shield (not shown). As with previous embodiments, the body utilizes sections $13a^{VII}$ which can be gripped by a user and squeezed together to cause the sections $13b^{VII}$ to expand radially outwardly and thereby cause the thread sections $14^{VII}$ to disengage from the threads of the section 2. The embodiment shown in FIG. 42 utilize a safety-shield (not shown) by virtue of the fact that it includes slots $17^{VII}$ that receive therein the legs of the safety-shield.

Figure 43:
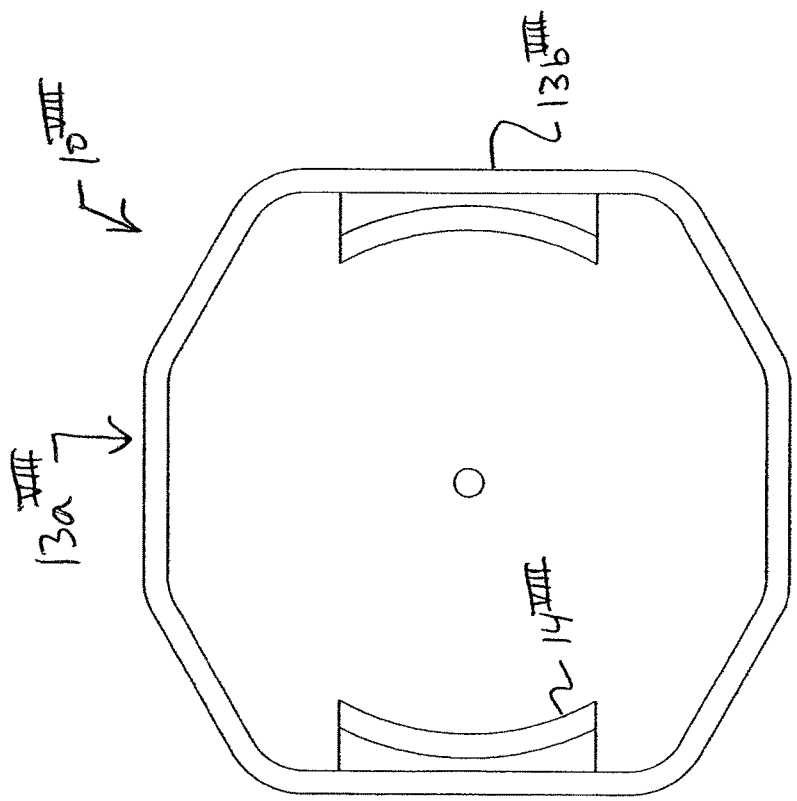
FIG. 43 shows a rear end view of another non-limiting embodiment of a pen needle or tip assembly according to the invention. In this embodiment, the pen needle body is even more rectangular-shaped than the shape shown in FIG. 41.

FIG. 43 shows a rear end view of another non-limiting embodiment of a pen needle or tip assembly according to the invention. In this embodiment, the body of the pen needle $10^{VIII}$ is more rectangular-shaped than the oval-shape shown in FIG. 3. As with previous embodiments, the body utilizes sections $13a^{VIII}$ which can be gripped by a user and squeezed together to cause the sections $13b^{VIII}$ to expand radially outwardly and thereby cause the thread sections $14^{VIII}$ to disengage from the threads of the section 2. The embodiment shown in FIG. 43 does not utilize a safety-shield.

Figure 44:
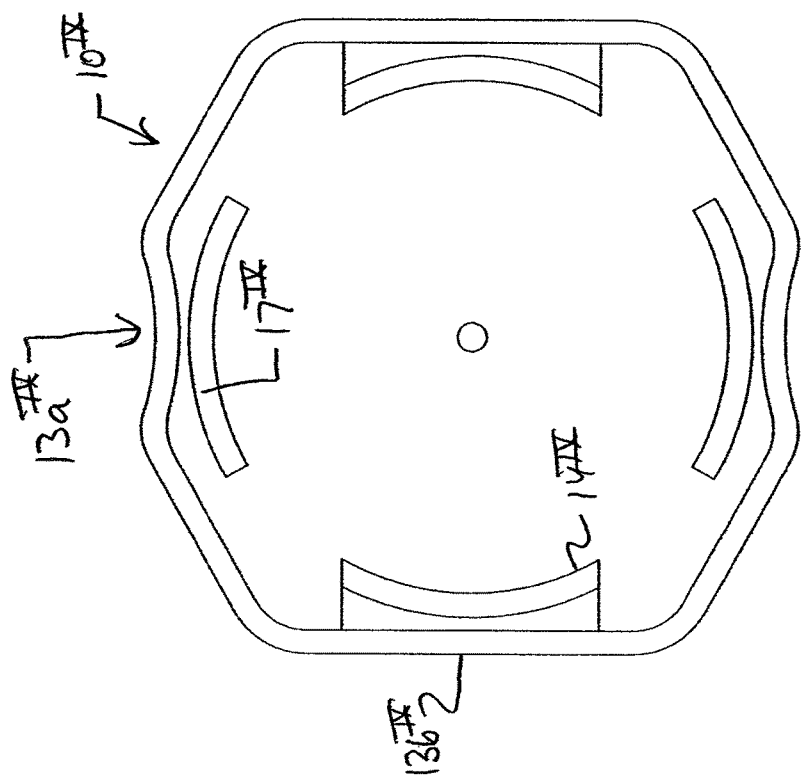
FIG. 44 shows a rear end view of another non-limiting embodiment of a pen needle or tip assembly according to the invention. In this embodiment, the pen needle body is made similar to that shown in FIG. 43 and is modified to utilize indented finger-receiving sections and a needle-shield (not shown) and utilizes slots that receive therein portions of the safety-shield.

FIG. 44 shows a rear end view of another non-limiting embodiment of a pen needle or tip assembly according to the invention. In this embodiment, the body of the pen needle $10^{IX}$ is similar to that shown in FIG. 43 except that it utilizes a safety-shield (not shown) and indented sections $13a^{IX}$. As with previous embodiments, the body utilizes sections $13a^{IX}$ which can be gripped (more easily because of the indented shape thereof) by a user and squeezed together to cause the sections $13b^{IX}$ to expand radially outwardly and thereby cause the thread sections $14^{IX}$ to disengage from the threads of the section 2. The embodiment shown in FIG. 44 utilize a safety-shield (not shown) by virtue of the fact that it includes slots $17^{IX}$ that receive therein the legs of the safety-shield.

FIG. 45 shows another non-limiting embodiment of a pen needle or tip assembly according to the invention. Like other embodiments, the embodiment utilizes a system $18^X/24^X$ for locking the safety-shield $20^V$ in a fully extended position so as to prevent re-use of the pen needle $10^X$. This embodiment also illustrates how the pen needle $10^X$ can be individually packaged. The packaging includes a simple removable sleeve PC". An optional removable seal RS can also 9 be utilized (not shown) similar to that used in FIGS. 31 and 32.

The cover PC'' can also have a mechanism, e.g., projections, (not shown) that allows the cover PC'' to be releasably retained on the tip $10^X$. The cover PC'' functions to protect the safety-shield $20^V$ and ensures that the safety-shield $20^V$ is not accidentally moved to the retracted position. In order to use the packaged pen needle $10^X$ shown in FIG. 45, the user can then install the pen needle $10^X$ onto the section 2 in any manner described herein. Then, the user can remove the protective cover PC'' and use the pen needle $10^X$ for injection. The user can then re-install the protective cover PC'' and then remove the pen needle $10^X$ from the section 2. However, this is not necessary if the safety-shield $20^V$ is in the fully extended position because members $24^X$ will be positioned and/or locked in a recess formed in the members $18^X$ and prevent distal movement of the safety-shield $20^V$. Instead, the user can simply remove the pen needle $10^X$ from the section 2 without the protective cover PC'' being installed thereon. The packaging system PC'' of this embodiment can be utilized on any of the herein disclosed embodiments using a safety-shield to the extent desirable.

Figure 46:
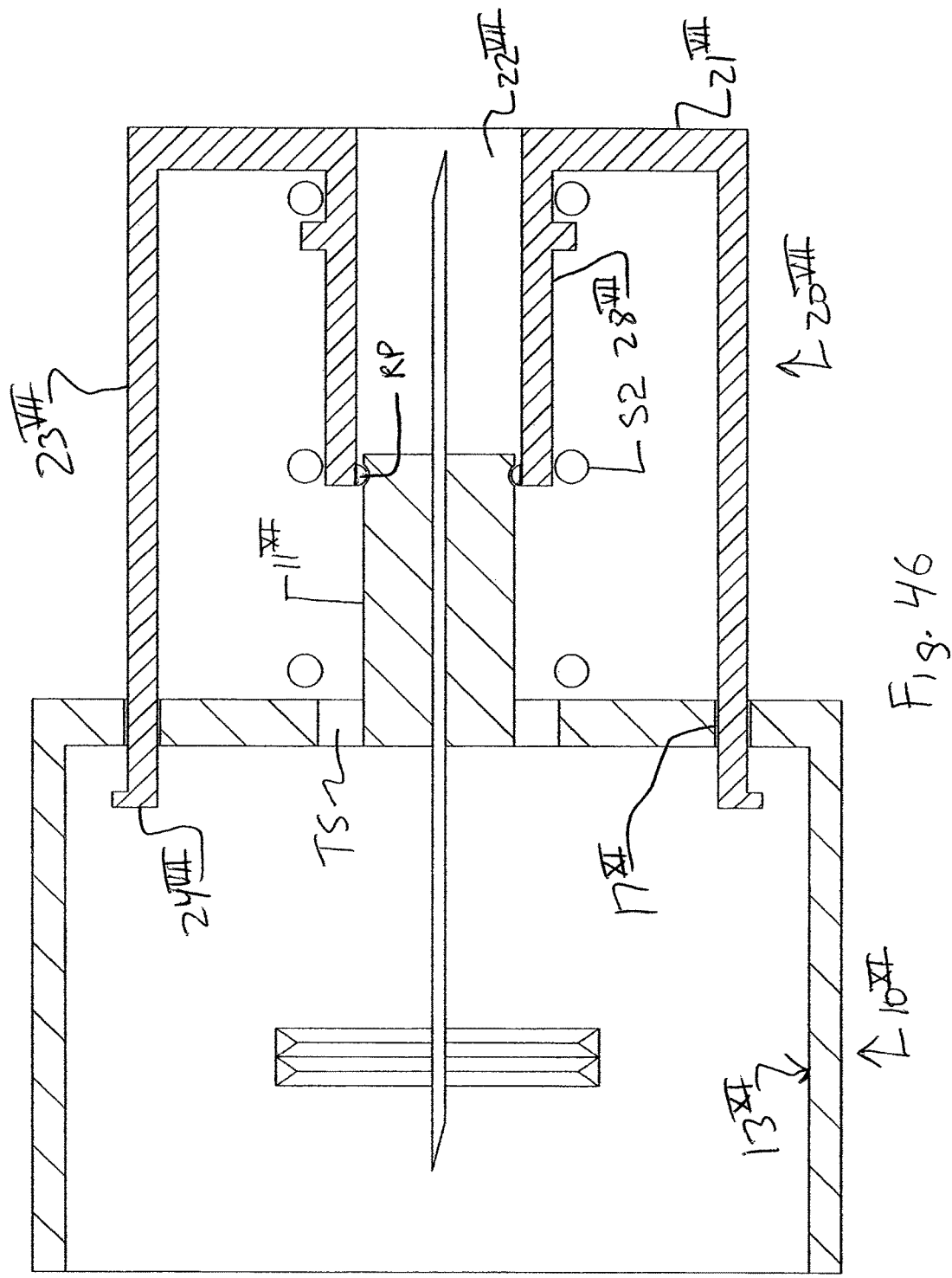
FIG. 46 shows a side cross-section view of another non-limiting embodiment of a pen needle or tip assembly according to the invention. The hollow needle is not shown in cross-section. This embodiment also utilizes a lockable safety-shield so as to prevent re-use of the pen needle and a system for releasably retaining the safety-shield in the initial or nearly-fully extended position. This system also prevents the safety-shield from moving from the fully extended position back to the initial position. The safety-shield is shown in an initial or nearly-fully extended position.
Figure 47:
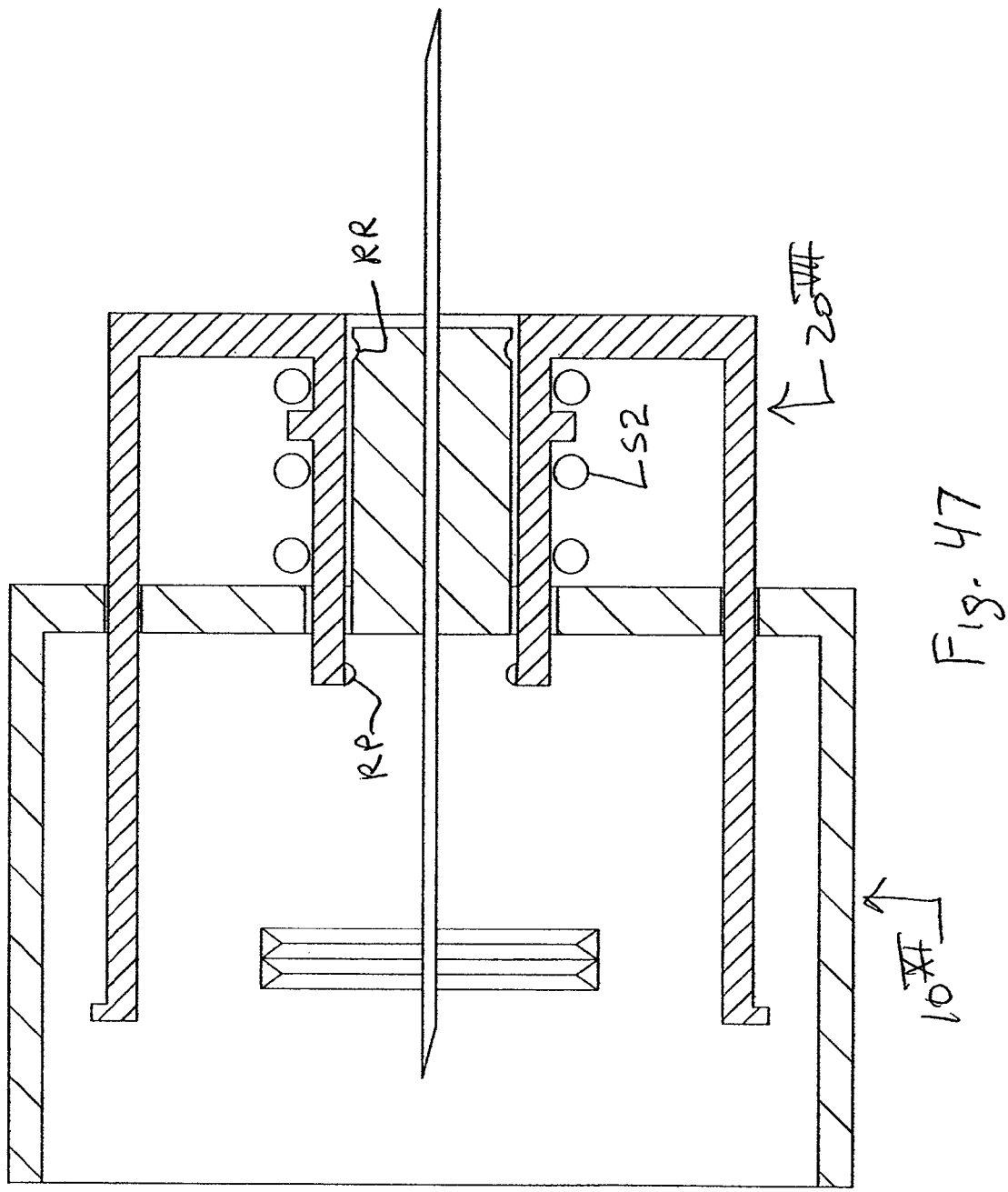
FIG. 47 shows a side cross-section view of the pen needle or tip assembly of FIG. 46. The safety-shield is shown in a using/injection or fully retracted position.
Figure 48:
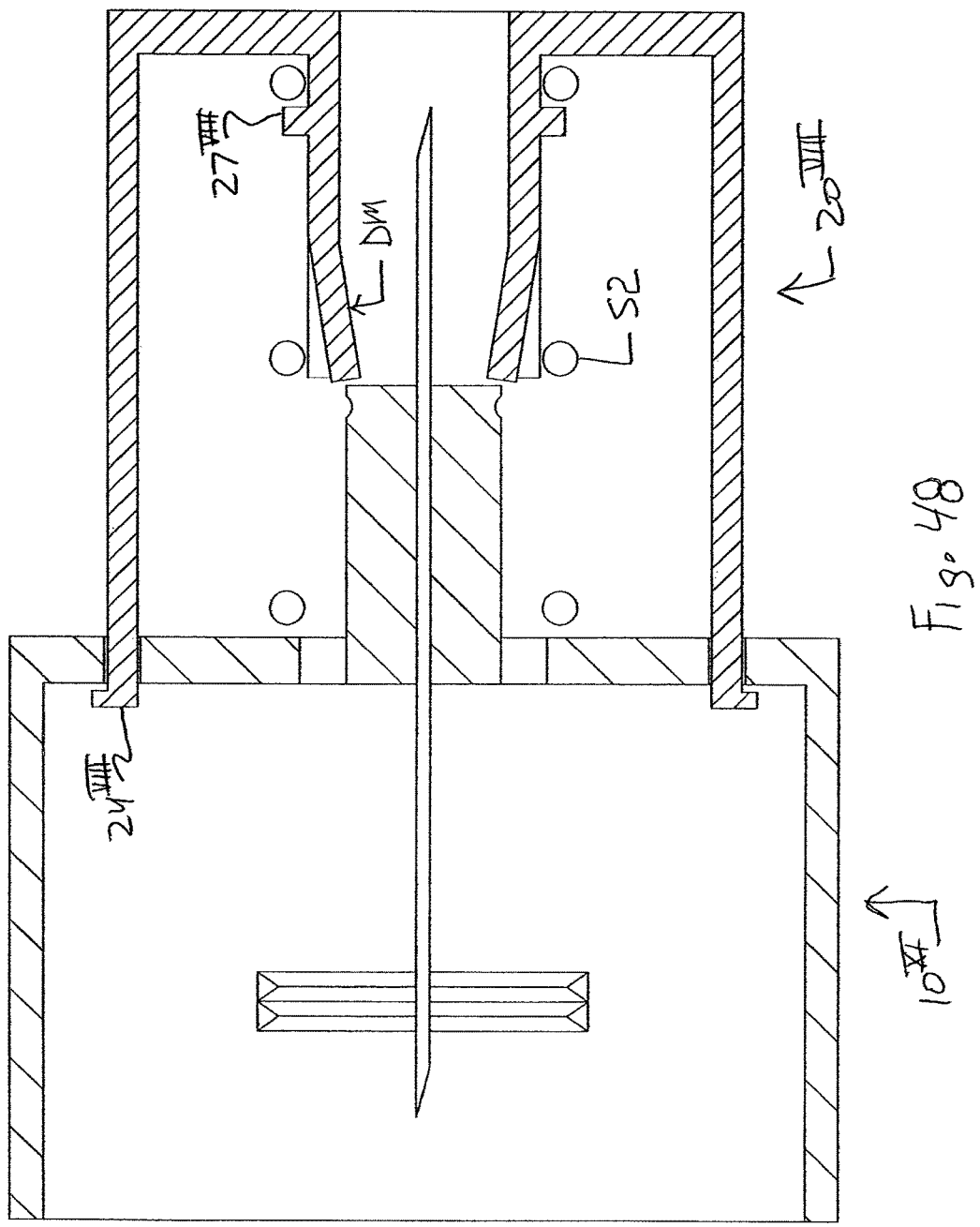
FIG. 48 shows a side cross-section view of another non-limiting embodiment of a pen needle or tip assembly according to the invention. The hollow needle is not shown in cross-section. This embodiment also utilizes a lockable safety-shield so as to prevent re-use of the pen needle and a system for releasably retaining the safety-shield in the initial or nearly-fully extended position. This system also prevents the safety-shield from moving from the fully extended position back to the initial position. The safety-shield is shown in the fully extended and locked position.
Figure 49:
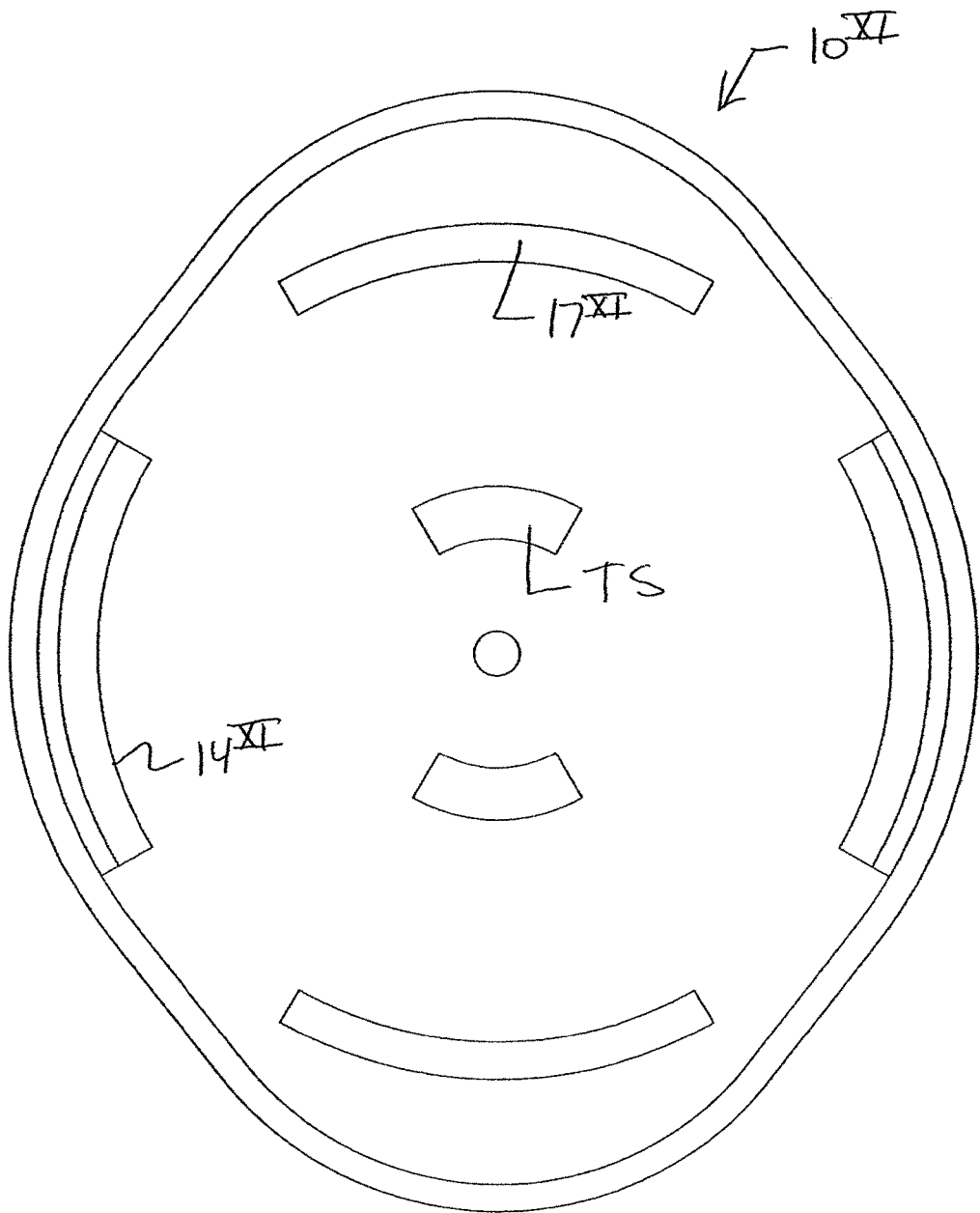
FIG. 49 shows a rear end view of the pen needle or tip assembly of FIG. 48 with the safety-shield removed.

FIGS. 46 and 47 show another non-limiting embodiment of a pen needle or tip assembly according to the invention. FIG. 22 shows a side cross-section view of the pen needle or tip $10^{XI}$ assembly which utilizes the main features of one or more previous embodiments including a safety-shield $20^{VII}$ and a spring S2 for biasing the shield $20^{VII}$ towards an extended position. The safety-shield $20^{VII}$ includes a generally circular front section $21^{VII}$ which (in the extended position) is sized and configured to extend out past the proximal end of the needle N and is configured to cover the needle N so that the user will be less likely to be pricked by the needle N. The safety-shield $20^{VII}$ also includes a generally circular through opening $22^{VII}$ which in this embodiment is enlarged and which allows the needle N to pass there through when it is retracted. The safety-shield $20^{VII}$ further also includes plural, e.g., two oppositely arranged, generally partially circular legs $23^{VII}$ which connect the section $21^{VII}$ to distal projections $24^{VII}$. Each semi-circular leg $23^{VII}$ is sized and configured to pass through and move within one of the partially circular slots $17^{XI}$ formed in the body $13^{XI}$ of the tip $10^{XI}$. Each projection $24^{VII}$ is larger, i.e., thicker, than the slot $17^{XI}$ and is sized and configured to limit and define the axial movement/position of the safety-shield $20^{VII}$ in the fully extended and locked position (see FIG. 46). As is apparent from FIGS. 46 and 47, when retaining projection RP arranged on a non-continuous flange $28^{VII}$ are releasably retained in a circumferential recess formed in the main support $11^{XI}$, the safety-shield $20^{VII}$ is in an initial and/or prior-use and nearly-fully extended position (see FIG. 46). Moreover, openings TS (which are semi-circular as shown in FIG. 49) allow the distal end of the distal portions of section $28^{VII}$ extend therein when the safety-shield $20^{VII}$ is moved to the retracted position (see FIG. 47). However, when each projection RP extends out past the proximal end of the support $11^{XI}$, the safety-shield $20^{VII}$ is in a fully extended and locked position (not shown but similar to that shown in FIG. 48)—thereby rendering the tip $10^{XI}$ single-use.

Figure 50:
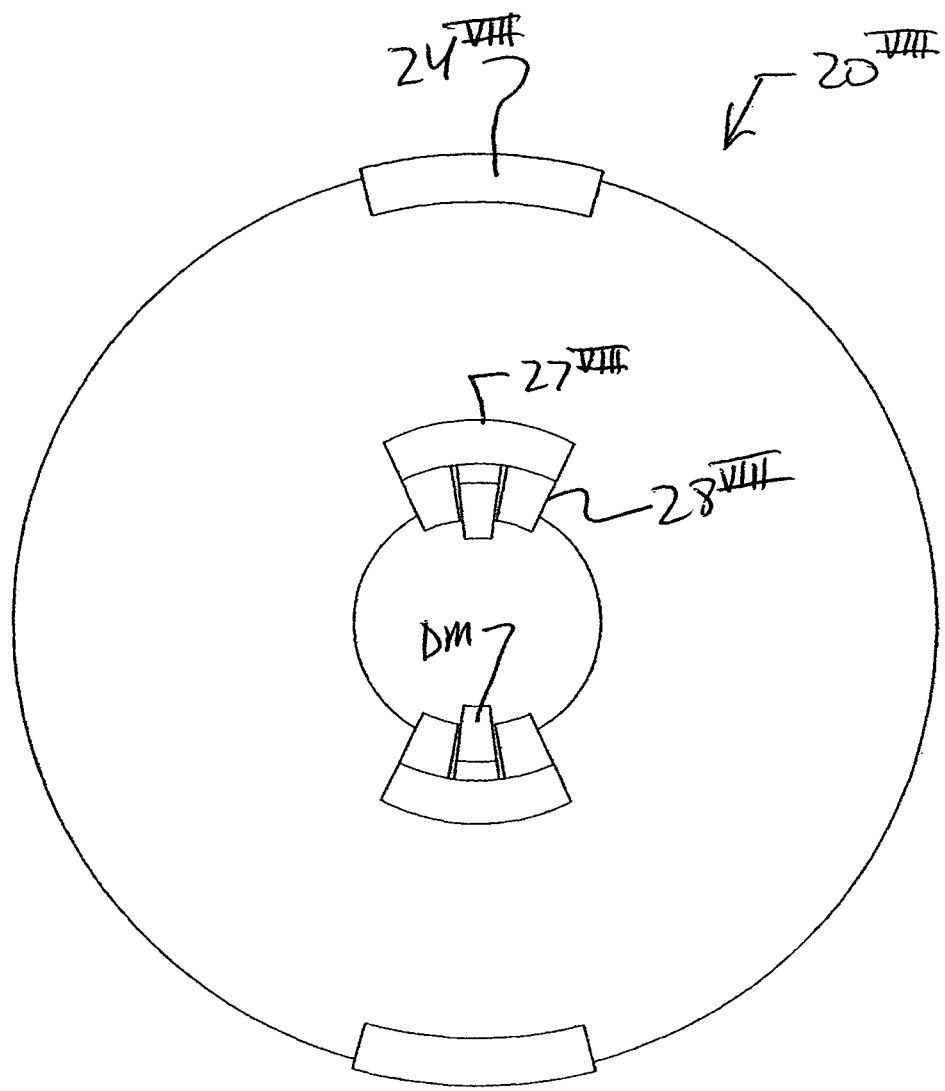
FIG. 50 shows a rear end view of the safety-shield used in the pen needle or tip assembly of FIG. 48.

FIG. 49 shows another non-limiting embodiment of a pen needle or tip assembly according to the invention. This embodiment is similar to that shown in FIGS. 46 and 47 except that the flange $28^{VIII}$ utilizes deflectable members DM whose free ends are releasably retained in the circumferential groove of the support $11^{XI}$. These members DM are arranged between the non-continuous flange $28^{VIII}$ (see FIG. 50) prevent the safety-shield $20^{VIII}$ from moving from the fully extended position shown in FIG. 48 back to an initial position (similar to that shown in FIG. 46).

Figure 52:
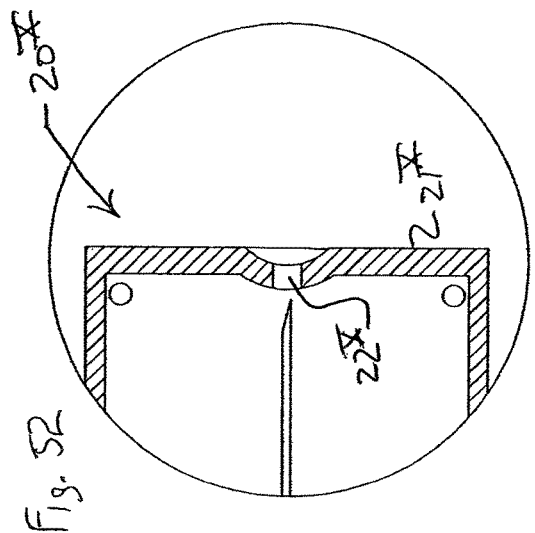
FIGS. 51-54 show partial cross-section views of additional non-limiting embodiments of safety shields having differently textured proximal surfaces, i.e., different surface configurations for contacting a user's skin.
Figure 54:
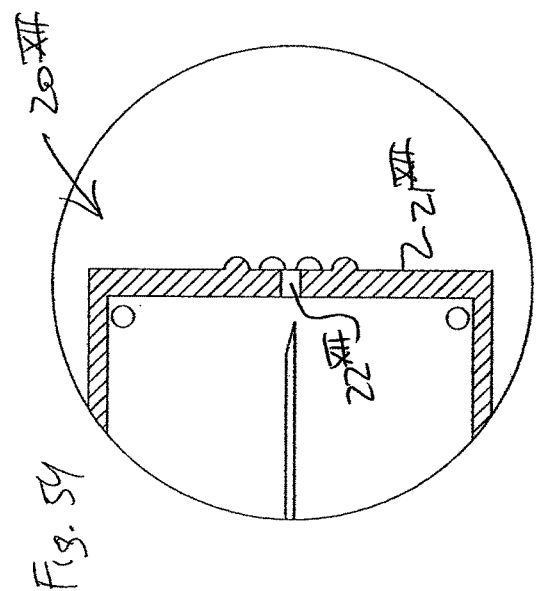
Figure 51:
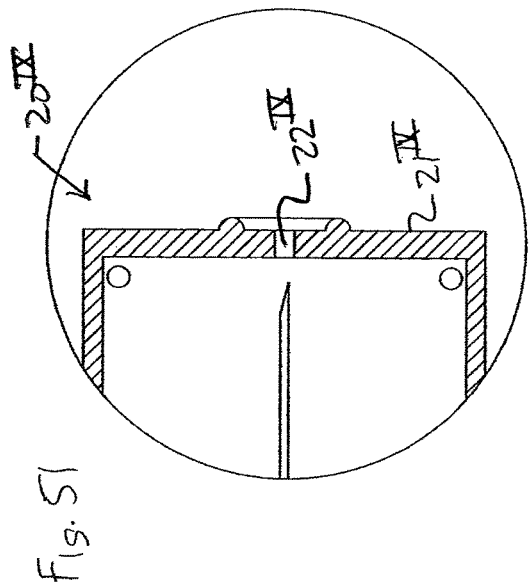
Figure 53:
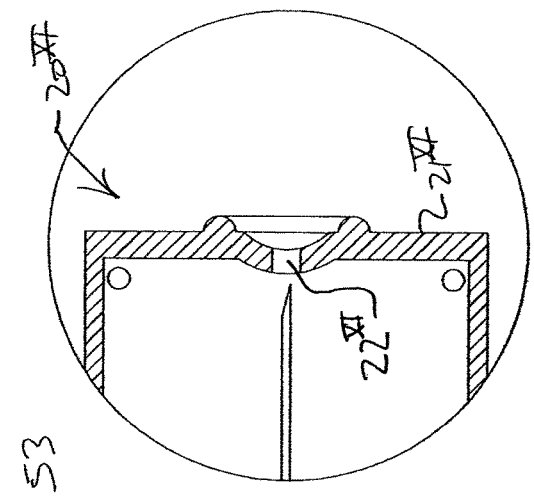
Figure 55:
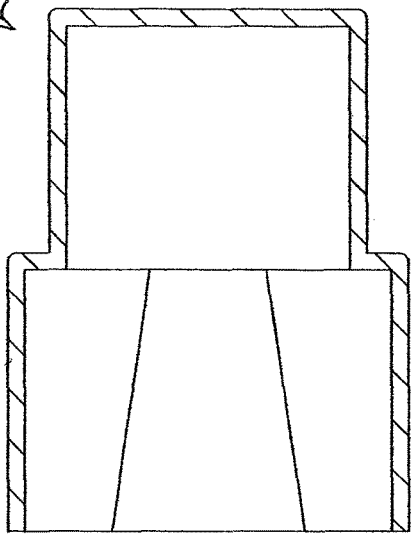
FIGS. 55-58 show side cross-section and rear views of a non-limiting embodiment of a front cover or outer cap which can be used on any of the herein disclosed oval-shaped pen needles.

FIGS. 51-54 show partial cross-section views of additional non-limiting embodiments of safety shields having differently textured proximal surfaces, i.e., different surface configurations for contacting a user's skin. In FIG. 51, the safety-shield $20^{IX}$ has a skin contacting surface $21^{IX}$ defined by a circular projection which surrounds the opening $22^{IX}$. In FIG. 52, the safety-shield $20^X$ has a skin contacting surface $21^X$ defined by a concave indentation which surrounds the opening $22^X$. In FIG. 53, the safety-shield $20^{XI}$ has a skin contacting surface $21^{XI}$ defined by both a circular projection and a concave indentation which surrounds the opening $22^{XI}$. In FIG. 54, the safety-shield $20^{XII}$ has a skin contacting surface $21^{XII}$ defined by a circular configuration separate projections which surrounds the opening $22^{XII}$. Any of these embodiments can be utilized on any of the herein disclosed embodiments using a safety-shield to the extent desirable.

Figure 57:
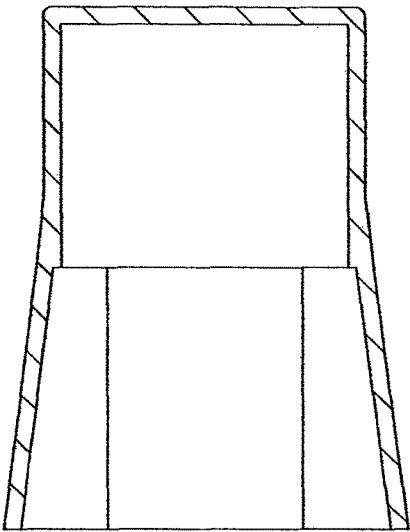
Figure 56:
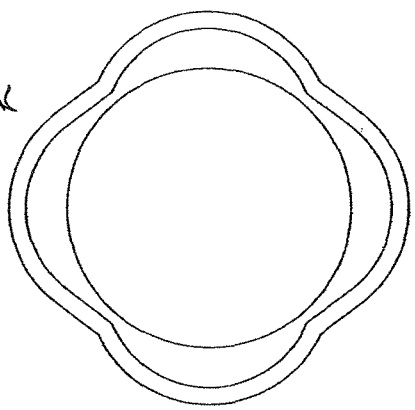
Figure 58:
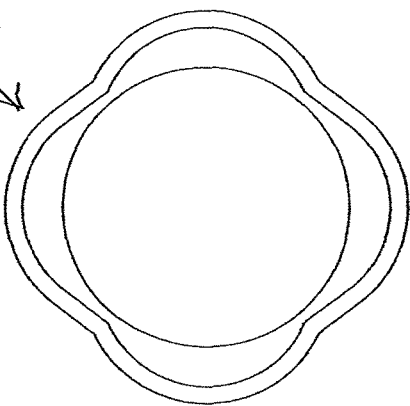

FIGS. 55-58 show a non-limiting embodiment of a front cover or outer cap PC''' which can be used on any of the herein disclosed oval-shaped pen needles. FIGS. 57 and 58 are rotated 90 degrees relative to FIGS. 55 and 56. The front cover PC''' can be removed from a respective pen needle and rotated 90 degrees and then reinstalled so that axial sliding on of the front cap PC''' causes the squeezing forces shown in FIG. 6 via a sliding-on motion.

The devices described herein can also utilize one or more features disclosed in prior art documents expressly incorporated by reference in pending U.S. patent application Ser. No. 11/616,195 (Publication No. 2008/0154192). This application and the documents expressly incorporated therein is hereby expressly incorporated by reference in the instant application. Furthermore, one or more of the various parts of the device can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:
1. An injection device tip comprising:
  a body configured to be removably connected to an injection device and having an internal space configured to receive therein a proximal end of the injection device;

a proximal wall of the body comprising an opening extending through the proximal wall and being sized and configured to receive therein a portion of a safety shield;
the proximal wall having a non-circular shape;
a distal end of the body having a non-circular shape; and
a needle having a portion extending into the internal space from the proximal wall and a portion projecting out from a proximal end of the body and being non-axially movably coupled to the proximal wall;
said portion extending into the internal space being structured and arranged to puncture a puncturable surface of the injection device when the body is installed on the injection device,
wherein the body has finger grippable flexible portions which can be deflected inwardly to cause release of an engagement between the body and the proximal end of the injection device so as to allow removal of the body from the proximal end of the injection device.

2. The tip of claim 1, further comprising at least one of:
a safety shield movably mounted to the proximal end of the body;
a safety shield arranged on the proximal end of the body; and
a safety shield is movable at least between an initial position and an extended position.

3. The tip of claim 2, wherein the initial position and the extended position each covers a free end of the needle.

4. The tip of claim 1, further comprising a safety shield movable at least between an initial position, a retracted position, and an extended position.

5. The tip of claim 4, wherein at least one of:
the initial position covers a free end of the needle and the retracted position exposes a free end of the needle;
the extended position covers a free end of the needle and the retracted position exposes a free end of the needle;
the initial position covers a free end of the needle, the retracted position exposes a free end of the needle, and the extended position prevents re-use of the tip; and
the retracted position exposes a free end of the needle and, in the extended position, the safety shield is one of locked and non-movably retained.

6. The tip of claim 1, wherein the needle is a single double-ended needle.

7. The tip of claim 1, wherein the body comprises at least one projection for engaging an external thread of the proximal end of the injection device.

8. The tip of claim 1, wherein, once installed, the tip threadably engages with the proximal end of the injection device.

9. The tip of claim 1, wherein the body comprises at least one partial internal thread section for engaging an external thread of the proximal end of the injection device.

10. The tip of claim 1, wherein the body comprises at least two oppositely arranged partial internal thread sections for engaging an external thread of the proximal end of the injection device.

11. The tip of claim 1, wherein the body is a one-piece member and is generally oval in shape.

12. The tip of claim 1, wherein the body includes an internal space between each of the flexible portions and the proximal end of the injection device and is generally non-circular in shape.

13. The tip of claim 1, wherein the body includes a single sidewall arranged to surround a proximal end of the injection device, said single sidewall comprising the flexible portions which can be deflected inwardly to cause release of an engagement between the body and the proximal end of the injection device and is generally non-circular in shape.

14. The tip of claim 1, further comprising an axially movable safety shield adapted to cover the portion projecting out from a proximal end of the body.

15. A method of removing the tip of claim 1, the method comprising:
installing the tip onto a proximal end of an injection device;
removing the tip by applying a squeezing force to opposite sides of the body.

16. A method of removing the tip of claim 1, the method comprising:
installing the tip onto a proximal end of an injection device;
utilizing an outer cover to remove the tip such that a narrower width section of the outer cover is utilizes to apply a squeezing force to opposite sides of the body.

17. The tip of claim 1, wherein the flexible portions are two oppositely arranged flexible portions arranged outside an imaginary circle defined by an outside surface of two opposite portions arranged between the two oppositely arranged flexible portions.

18. The tip of claim 1, wherein the body is at least one of:
is generally oval in shape;
is generally rectangular in shape; and is generally square in shape.

19. The tip of claim 1, wherein the body has a single sidewall arranged to surround a proximal end of the injection device, said single sidewall being non-circular in shape.

20. A pre-filled injection device comprising:
a pre-filled injection device body;
a removable pen needle installed on the pre-filled injection device body;
said pen needle comprising a body, a wall and a needle having first and second ends arranged on opposite sides of the wall;
a safety shield having a portion that passes through an opening in the wall and extends into an internal space of the body;
said safety shield being movable at least between a retracted position and an extended position covering the second end of the needle;
said portion of the safety shield extending into the internal space and being movable back past a proximal end of the pre-filled injection device when the pen needle is installed on the proximal end of the pre-filled injection device;
said internal space being sized and configured to removably receive therein the proximal end of the pre-filled injection device,
wherein the body has flexible portions which can be deflected inwardly to cause release of an engagement between the body and the proximal end of the pre-filled injection device.

21. The device of claim 20, wherein an open distal end of the body of the pen needle at least one of:
has two oppositely arranged flexible portions arranged outside an imaginary circle defined by an outside surface of two opposite portions arranged between the two oppositely arranged flexible portions;
is generally oval in shape;
is generally rectangular in shape; is generally square in shape; and is non-circular in shape.

22. A pen needle comprising:
a body having an open distal end configured to be removably connected to a proximal end of an injection device;
the body having a non-circular cross-section in a side-wall area surrounding the proximal end of the injection device;
a needle having a puncturing portion projecting from a proximal end of the body and an intermediate portion non-axially movably coupled to a wall of the body;
the wall having a non-circular cross-section and arc-shaped openings,
the body comprising a finger grippable deflectable or flexible side-wall portion arranged behind the wall which can be deflected inwardly to cause release of an engagement between the body and the proximal end of the injection device;
the body defining a space between the deflectable or flexible side-wall portion and the proximal end of the injection device when the proximal end is disposed within the body;
a needle shield having portions that pass through the arc-shaped openings of the wall;
and said space being changed when a user causes release of the engagement between the body and
the proximal end of the injection device,
wherein deflection of the side-wall portions changes a shape of the open distal end of the body.

23. The pen needle of claim 22, wherein the needle shield is axially movable at least between an initial position, a retracted position and a locked extended position.

24. An injection device tip comprising: a body configured to be removably connected to an injection device and having an internal space configured to receive therein a proximal end of the injection device; a proximal wall of the body comprising an opening; the proximal wall having a non-circular shape; a distal end of the body having a non-circular shape; and
a needle having a portion extending into the internal space from the proximal wall and a portion projecting out from a proximal end of the body and being non-axially movably coupled to the proximal wall;
said portion extending into the internal space being structured and arranged to puncture a puncturable surface of the injection device when the body is installed on the injection device,
wherein the body has finger grippable flexible portions which can be deflected inwardly to cause release of an engagement between the body and the proximal end of the injection device so as to allow removal of the body from the proximal end of the injection device, and
further comprising a safety shield having a portion that extends through the opening and into an internal space located within the body and being movably mounted to the body and being adapted to cover the portion projecting out from a proximal end of the body.

25. A pen needle comprising:
a body having an open distal end configured to be removably connected to a proximal end of an injection device;
the body having a non-circular cross-section in an area surrounding the proximal end of the injection device;
a needle having a puncturing portion projecting from a proximal end of the body and an intermediate portion non-axially movably coupled to a wall of the body;
the wall having openings;
the body comprising finger grippable deflectable or flexible side-wall portions arranged behind the wall which can be deflected inwardly to cause release of an engagement between the body and the proximal end of the injection device;
a one-piece needle shield having portions that pass through the openings of the wall;
and the one-piece needle shield being axially movable at least between an initial position, a retracted position and a locked extended position,
wherein deflection of the side-wall portions changes a shape of the open distal end of the body.

* * * * *